United States Patent [19]

Tsushima et al.

[11] Patent Number: 4,840,971

[45] Date of Patent: Jun. 20, 1989

[54] NOVEL ETHER COMPOUND, A PROCESS FOR MANUFACTURING THE SAME, A COMPOSITION CONTAINING THE SAME AND A USE THEREOF

[75] Inventors: Kazunori Tsushima, Nishinomiya, Japan; Noritada Matsuo, Rochester, N.Y.; Yoo Tanabe, Toyonaka, Japan; Toshihiko Yano, Ikoma, Japan; Masachika Hirano, Osaka, Japan

[73] Assignee: Sumitomo Chemical Company, Limited, Osaka, Japan

[21] Appl. No.: 33,245

[22] Filed: Apr. 2, 1987

[30] Foreign Application Priority Data

Apr. 7, 1986 [JP] Japan .................... 61-79664
Aug. 16, 1986 [JP] Japan .................... 61-191833
Feb. 10, 1987 [JP] Japan .................... 61-28575

[51] Int. Cl.$^4$ .......................... A61K 31/085
[52] U.S. Cl. .................. 514/721; 568/637; 568/39; 568/659; 568/661; 568/649; 568/812; 568/808; 568/637; 546/293; 546/302; 546/312; 564/433; 549/445; 549/440; 514/720; 514/658; 514/464; 514/466; 514/345; 514/352
[58] Field of Search ............... 568/39, 636, 637, 659, 568/661; 564/43; 514/720, 721

[56] References Cited

U.S. PATENT DOCUMENTS

| | | | |
|---|---|---|---|
| 2,715,144 | 8/1955 | Ruh | 568/376 |
| 4,073,812 | 2/1987 | Bull et al. | 568/637 |
| 4,397,864 | 8/1983 | Nakatani et al. | 568/68 |
| 4,664,698 | 5/1987 | Tsuskima et al. | 568/637 |
| 4,678,811 | 7/1987 | Frank et al. | 568/39 |

FOREIGN PATENT DOCUMENTS

| | | | |
|---|---|---|---|
| 0094085 | 11/1983 | European Pat. Off. | 71/100 |
| 0104908 | 4/1984 | European Pat. Off. | 71/100 |
| 0211561 | 2/1987 | European Pat. Off. | 71/100 |
| 715657 | 12/1931 | France | 568/376 |
| 58-52202 | 3/1983 | Japan | 568/637 |
| 58-55402 | 4/1983 | Japan | 568/637 |
| 1419132 | 12/1975 | United Kingdom | 71/122 |

OTHER PUBLICATIONS

Journal of the American Chemical Society, vol. 92, No. 4, Feb. 25, 1970, U.S., G. Barth et al.: "Optical Rotary Dispersion Studies, CXVII, Absolute Configurational Assignments of Some Alpha-Substituted Phenylacetic Acids by Circular Dichroism Measurements".

Journal of Organic Chemistry, vol. 32, Sep. 1967, pp. 2797–2798, C. Aaron et al.: "The Resolution and Configuration of Alpha-Substituted Phenylacetic Acids".

Primary Examiner—James H. Reamer
Attorney, Agent, or Firm—Stevens, Davis, Miller & Mosher

[57] ABSTRACT

An ether compound represented by the following general formula (I), its produciton method and an insecticidal and/or acaricidal composition containing it as an active ingredient:

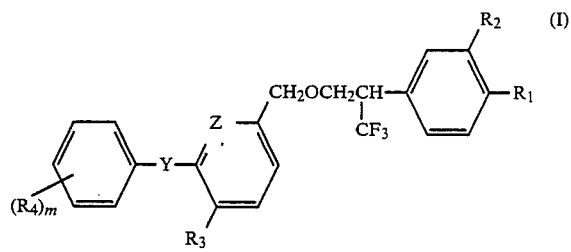

wherein $R_1$ and $R_2$, which may be identical or different, represent a hydrogen or halogen atom or a lower alkyl, lower haloalkyl, lower alkoxyl, lower haloalkoxyl, lower alkenyl or lower alkenyloxyl group, or represent, taken together, methylenedioxy, lower alkylene, ethyleneoxy or lower alkylethyleneoxy group; $R_3$ represents a hydrogen or fluorine atom; $R_4$ represents a hydrogen or halogen atom or a lower alkyl, lower haloalkyl, lower alkoxyl or lower haloalkoxyl group; m represents an integer of 1 or 2; Y represents an oxygen or sulfur atom or a group represented by the formula —$CH_2$— or —NH—; and Z represents a nitrogen atom or a group represented by the formula —CH=, and its starting materials.

6 Claims, No Drawings

NOVEL ETHER COMPOUND, A PROCESS FOR MANUFACTURING THE SAME, A COMPOSITION CONTAINING THE SAME AND A USE THEREOF

The present invention relates to a novel ether compound and its optical isomer represented by the general formula (I) described below, its production method and an insecticidal and acaricidal composition containing it as an active ingredient:

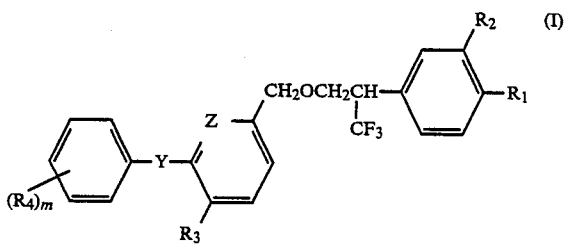

wherein $R_1$ and $R_2$, which may be identical or different, represent a hydrogen or halogen (e.g. fluorine, chlorine, bromine) atom or an alkyl (e.g. $C_{1-5}$ lower alkyl), haloalkyl (e.g. $C_{1-5}$ lower alkyl substituted with fluorine, chlorine or bromine atom), alkoxyl (e.g. $C_{1-5}$ lower alkoxyl), haloalkoxyl (e.g. $C_{1-5}$ lower alkoxyl substituted with fluorine, chlorine or bromine atom, alkenyl (e.g. $C_{2-5}$ lower alkenyl) or alkenyloxyl (e.g. $C_{2-5}$ lower alkenyloxyl) group, or represent, taken together, methylenedioxy, alkylene (e.g. $C_{3-4}$ lower alkylene), athylenoxy or alkylethylenoxy (e.g. ethylenoxy substituted with $C_{1-5}$ lower alkyl) group; $R_3$ represents a hydrogen fluorine atom; $R_4$ represents a hydrogen or halogen (e.g. fluorine, chlorine, bromine) atom or an alkyl (e.g. $C_{1-5}$ lower alkyl), haloalkyl (e.g. $C_{1-5}$ lower alkyl substituted with fluorine, chlorine or bromine atom), alkoxyl (e.g. $C_{1-5}$ lower alkoxyl) or haloalkoxyl (e.g. $C_{1-5}$ lower alkoxyl substituted with fluorine, chlorine or bromine atom) group; m represents an integer of 1 or 2; Y represents an oxygen or sulfur atom or a group represented by the formula —$CH_2$— or —NH—; and Z represents a nitrogen atom or a group represented by the formula —CH=.

The present inventors studied for the purpose of developing compounds having excellent insecticidal and-/or acaricidal activity, and as a result, found that the present compound represented by the foregoing general formula (I) has characteristics that (1) it has a high insecticidal and acaricidal effect and (2) its insecticidal effect on insect pests resistant to organophosphorous compounds or carbamates is also excellent. The present inventors thus attained to the present invention.

As examples of harmful pests for which the present compound is particularly effective, there are given for example Hemiptera such as planthoppers, leaf-hoppers, aphids, bugs, white flies, etc.: Lepidoptera such as diamond-back moth (*Plutella xylostella*), rice stem borer (*Chilo suppressalis*), leafrollers, armyworms and cutworms, etc.; Diptera such as common mosquito (*Culex pipiens pallens*), Anopheles species, Aedes species, housefly (*Musca domestica*), etc.; Dictyoptera such as German cockroach (*Blattella germanica*), Periplaneta species, etc.; Hymenoptera, Thysanoptera, Coleoptera, Orthoptera and Acarina such as carmine spider mite (*Tetranychus cinnabarinus*), two-spotted spider mite (*Tetranychus ultica*), citrus red mite (*Panonychus citri*), etc.

In the present compound represented by the foregoing general formula (I), the compound wherein $R_1$ and $R_2$ represent a hydrogen or halogen atom or an lower alkyl, lower haloalkyl, lower alkoxyl, lower haloalkoxyl, lower alkenyl or lower alkenyloxyl group, or represent, taken together, a methylenedioxy or trimethylene group; $R_3$ represents a hydrogen or flourine atom; $R_4$, which is at p-position, represents a hydrogen, or halogen atom or a lower alkyl or lower haloalkyl group; m represents an integer of 1; Y represents an oxygen atom or a group represented by the formula —NH—; and Z represents a group represented by the formula —CH= is preferable. And the compound wherein $R_1$ represents a fluorine, chlorine or bromine atom or a lower alkyl, lower alkoxyl, lower haloalkoxyl or trifluoromethyl group; $R_2$ represents a hydrogen atom; $R_3$ represents a hydrogen or fluorine atom; $R_4$, which is at p-position, represents a hydrogen, fluorine, chlorine or bromine atom or a methyl or trifluoromethyl group; m represents an integer of 1; Y represents an oxygen atom; and Z represents a group represented by the formula —CH= is more preferable.

The ether compound represented by the general formula (I) can be produced, for example, by reacting the compound represented by the general formula (II),

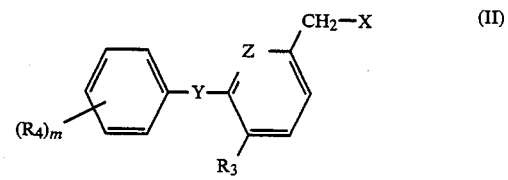

wherein $R_3$, $R_4$, m, Y and Z have the same meanings as described above, and X represents a halogen (e.g. chlorine or bromine) atom, with an alcohol compound represented by the general formula (III)

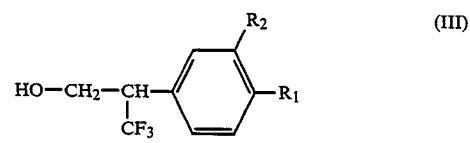

wherein $R_1$ and $R_2$ have the same meanings as described above, in the presence of a base.

More particularly, the above either compound (I) can be produced by reacting the compound represented by the general formula (II) with the alcohol compound represented by the general formula (III), in the presence of a base (e.g. sodium hydride, potassium hydride, lithium hydride, potassium t-butoxide, sodium hydroxide, potassium hydroxide, potassium fluoride, cesium fluoride) in an inert solvent (e.g. a polar aprotic solvent such as dimethylformamide (DMF), dimethylsulfoxide, dimethylacetamide and 1,3-dimethyl-2-imidazolidinone; an ether solvent such as tetrahydrofuran (THF), 1,4-dioxane and ethyleneglycol dimethyl ether; a hydrocarbon solvent such as n-hexane, benzene, toluene and xylene; water) for 1 to 72 hours at a temperature of from ice-cooling condition to heating condition. The reaction can be performed in the presence of a phase-transfer catalyst (e.g. a crown ether; a quarterly organic ammonium salt; a phosphonium salt).

The ether compound of the present invention represented by the formula (I) has optical isomers due to the asymmetric carbon on the benzyl group substituted with trifluoromethyl group, and these optical isomers, for example, can be obtained by the separation of a mixture of the enantiomers using column chromatography packed with an appropriate optically active stationary phase.

Examples of the ether compound which can be produced by the above method will be given below:

2-(4-Ethoxyphenyl)-3,3,3-triflouropropyl 3-phenoxybenzyl ether
2-(4-Ethoxyphenyl)-3,3,3-triflouropropyl 4-fluoro-3-phenoxybenzyl ether
2-(4-Ethoxyphenyl)-3,3,3-triflouropropyl 4-fluoro-3-anilinobenzyl ether
2-(4-Ethoxyphenyl)-3,3,3-triflouropropyl 4-fluoro-3-(4-fluoroanilino)benzyl ether
2-(4-Ethoxyphenyl)-3,3,3-triflouropropyl 4-fluoro-3-(4-methylanilino)benzyl ether
2-(4-Ethoxyphenyl)-3,3,3-triflouropropyl 3-(3,4-difluorophenoxy)benzyl ether
2-(4-Ethoxyphenyl)-3,3,3-trifluoropropyl 4-fluoro-3-(2,4-difluorophenoxy)benzyl ether
2-(4-Ethoxyphenyl)-3,3,3-trifluoropropyl 4-fluoro-3-(4-fluorophenoxy)benzyl ether
2-(4-Ethoxyphenyl)-3,3,3-trifluoropropyl 4-fluoro-3-(4-bromophenoxy)benzyl ether
2-(4-Ethoxyphenyl)-3,3,3-trifluoropropyl 4-fluoro-3-(4-chlorophenoxy)benzyl ether
2-(4-Ethoxyphenyl)-3,3,3-trifluoropropyl 3-(4-bromophenoxy)benzyl ether
2-(4-Ethoxyphenyl)-3,3,3-trifluoropropyl 3-(4-chlorophenoxy)benzyl ether
2-(4-Ethoxyphenyl)-3,3,3-trifluoropropyl 3-(4-fluorophenoxy)benzyl ether
2-(4-Ethoxyphenyl)-3,3,3-trifluoropropyl 4-fluoro-3-(4-methylphenoxy)benzyl ether
2-(4-Ethoxyphenyl)-3,3,3-trifluoropropyl 6-phenoxypyridin-2-ylmethyl ether
2-(4-Ethoxyphenyl)-3,3,3-trifluoropropyl 5-fluoro-6-phenoxypyridin-2ylmethyl ether
2-(4-Methoxyphenyl)-3,3,3-trifluoropropyl 3-phenoxybenzyl ether
2-(4-Methoxyphenyl-3,3,3-trifluoropropyl 4-fluoro-3-phenoxybenzyl ether
2-(4-n-Propoxyphenyl)-3,3,3-trifluoropropyl 4-fluoro-3-phenoxybenzyl ether
2-(4-i-Propoxyphenyl)-3,3,3-trifluoropropyl 4-fluoro-3-phenoxybenzyl ether
2-(4-i-Propoxyphenyl)-3,3,3-trifluoropropyl 3-phenoxybenzyl ether
2-(4-n-Propoxyphenyl)-3,3,3-trifluoropropyl 4-fluoro-3-anilinobenzyl ether
2-(4-Fluorophenyl)-3,3,3-trifluoropropyl 4-fluoro-3-phenoxybenzyl ether
2-(4-Fluorophenyl)-3,3,3-trifluoropropyl 3-phenoxybenzyl ether
2-(4-Fluorophenyl)-3,3,3-trifluoropropyl 3-(4-chlorophenoxy)benzyl ether
2-(4-Fluorophenyl)-3,3,3-trifluoropropyl 3-(4-bromophenoxy)benzyl ether
2-(4-Fluorophenyl)-3,3,3-trifluoropropyl 4-fluoro-3-(4-bromophenoxy)benzyl ether
2-(4-Fluorophenyl)-3,3,3-trifluoropropyl 4-fluoro-3-(3,4-dimethylphenoxy)benzyl ether
2-(4-Fluorophenyl)-3,3,3-trifluoropropyl 6-phenoxypyridin-2-ylmethyl ether
2-(4-Fluorophenyl)-3,3,3-trifluoropropyl 4-fluoro-3-anilinobenzyl ether
2-(4-Chlorophenyl)-3,3,3-trifluoropropyl 4-fluoro-3-phenoxybenzyl ether
2-(4-Chlorophenyl)-3,3,3-trifluoropropyl 3-phenoxybenzyl ether
2-(4-Chlorophenyl)-3,3,3-trifluoropropyl 4-fluoro-3-(4-bromophenoxy)benzyl ether
2-(4-Bromophenyl)-3,3,3-trifluoropropyl 4-fluoro-3-phenoxybenzyl ether
2-(4-Bromophenyl)-3,3,3-trifluoropropyl 3-phenoxybenzyl ether
2-(4-Methylphenyl)-3,3,3-trifluoropropyl 3-phenoxybenzyl ether
2-(4-Methylphenyl)-3,3,3-trifluoropropyl 4-fluoro-3-phenoxybenzyl ether
2-(4-Ethylphenyl)-3,3,3-trifluoropropyl 4-fluoro-3-phenoxybenzyl ether
2-(4-Ethylphenyl)-3,3,3-trifluoropropyl 3-phenoxybenzyl ether
2-(4-n-Propylphenyl)-3,3,3-trifluoropropyl 4-fluoro-3-phenoxybenzyl ether
2-(4-i-Propylphenyl)-3,3,3-trifluoropropyl 4-fluoro-3-phenoxybenzyl ether
2-(4-i-Propenylphenyl)-3,3,3-trifluoropropyl 4-fluoro-3-phenoxybenzyl ether
2-(4-t-Butyphenyl)-3,3,3-trifluoropropyl 4-fluoro-3-phenoxybenzyl ether
2-(4-Vinylphenyl)-3,3,3-trifluoropropyl 4-fluoro-3-phenoxybenzyl ether
2-(4-Trifluoromethylphenyl)-3,3,3-trifluoropropyl 3-phenoxybenzyl ether
2-(4-Trifluoromethylphenyl)-3,3,3-trifluoropropyl 4-fluoro-3-phenoxybenzyl ether
2-(4-Trifluoromethylphenyl)-3,3,3-trifluoropropyl 3-(4-chlorophenoxy)benzyl ether
2-(4-Trifluoromethylphenyl)-3,3,3-trifluoropropyl 4-fluoro-3-anilinobenzyl ether
2-(4-Trifluoromethylphenyl)-3,3,3-trifluoropropyl 5-fluoro-6-phenoxypyridin-2-ylmethyl ether
2-(4-Trifluoromethylphenyl)-3,3,3-trifluoropropyl 4-fluoro-3-(4-fluorophenoxy)benzyl ether
2-(4-Difluoromethoxyphenyl)-3,3,3-trifluoropropyl 4-fluoro-3-phenoxybenzyl ether
2-(4-Difluoromethoxyphenyl)-3,3,3-trifluoropropyl 3-phenoxybenzyl ether
2-(4-Difluoromethoxyphenyl)-3,3,3-trifluoropropyl 4-fluoro-3-anilinobenzyl ether
2-(4-Difluoromethoxyphenyl)-3,3,3-trifluoropropyl 6-phenoxypyridin-2-ylmethyl ether
2-(4-Difluoromethoxylphenyl)-3,3,3-trifluoropropyl 4-fluoro-3-(4-bromophenoxy)benzyl ether
2-(4-(2,2,2-Trifluoroethoxy)phenyl)-3,3,3-trifluoropropyl 3-phenoxybenzyl ether
2-(4-(2,2,2-Trifluoroethoxy)phenyl)-3,3,3-trifluoropropyl 4-fluoro-3-phenoxybenzyl ether
2-(4-(2-Propenyl)phenyl)-3,3,3-trifluoropropyl 4-fluoro-3-phenoxybenzyl ether
2-(4-(2-Propenyloxy)phenyl)-3,3,3-trifluoropropyl 3-phenoxybenzyl ether
2-(4-(2-Propenyl)phenyl)-3,3,3-trifluoropropyl 3-phenoxybenzyl ether
2(4-n-Propoxyphenyl)-3,3,3-trifluoropropyl 3-phenoxybenzyl ether
2-(4-Ethoxyphenyl)-3,3,3-trifluoropropyl 3-(4-ethylphenoxy)benzyl ether
2-(4-(2-Propenyloxy)phenyl)-3,3,3-trifluoropropyl 4-fluoro-4-phenoxybenzyl ether 2-(3,4-Difluorophenyl)-3,3,3-trifluoropropyl 4-fluoro-3-phenoxybenzyl ether
2-(3,4-Dichlorophenyl)-3,3,3-trifluoropropyl 4-fluoro-3-phenoxybenzyl ether
2-(3,4-Dimethylphenyl)-3,3,3-trifluoropropyl 4-fluoro-3-phenoxybenzyl ether
2-(3,4-Dimethoxyphenyl)-3,3,3-trifluoropropyl 4-fluoro-3-phenoxybenzyl ether
2-(3-Chloro-4-ethoxyphenyl)-3,3,3-trifluoropropyl 3-phenoxybenzyl ether
2-(3-Chloro-4-ethoxyphenyl)-3,3,3-trifluoropropyl 3-(4-fluorophenoxy)benzyl ether
2-(3-Chloro-4-ethoxyphenyl)-3,3,3-trifluoropropyl 4-fluoro-3-phenoxybenzyl ether
2-(3,4-Methylenedioxyphenyl)-3,3,3-trifluoropropyl 4-fluoro-3-phenoxybenzyl ether
2-(3,4-Methylenedioxyphenyl)-3,3,3-trifluoropropyl 3-phenoxybenzyl ether
2-(3,4-Methylenedioxyphenyl)-3,3,3-trifluoropropyl 4-fluoro-3-anilinobenzyl ether
2-(3,4-Methylenedioxylphenyl)-3,3,3-trifluoropropyl 5-fluoro-6-phenoxypyridin-2-ylmethyl ether
2-(4-Bromophenyl)-3,3,3-trifluoropropyl 3-(4-fluorophenoxy)benzyl ether
2-(4-Bromophenyl)-3,3,3-trifluoropropyl 4-fluoro-3-(4-chlorophenoxy)benzyl ether
2-(4-t-Butylphenyl)-3,3,3-trifluoropropyl 3-phenoxybenzyl ether
2-(4-Ethoxyphenyl)-3,3,3-trifluoropropyl 4-fluoro-3-(3-methylphenoxy)benzyl ether
2-(4-Bromophenyl)-3,3,3-trifluoropropyl 3-(4-chlorophenoxy)benzyl ether
2-(3-Methoxyphenyl)-3,3,3-trifluoropropyl 4-fluoro-3-phenoxybenzyl ether
2-(3-Methylphenyl)-3,3,3-trifluoropropyl 3-phenoxybenzyl ether
2-(3-Methylphenyl)-3,3,3-trifluoropropyl 4-fluoro-3-phenoxybenzyl ether
2-(3-Trifluoromethylphenyl)-3,3,3-trifluoropropyl 3-phenoxybenzyl ether
2-(3-Trifluoromethylphenyl)-3,3,3-trifluoropropyl 4-fluoro-3phenoxybenzyl ether
2-(3-Trifluoromethylphenyl(-3,3,3-trifluoropropyl 4-fluoro-3-anilinobenzyl ether
2-(3-Fluorophenyl)-3,3,3-trifluoropropyl 3-phenoxybenzyl ether
2-(3-Fluorophenyl)-3,3,3-trifluoropropyl 4-fluoro-3-phenoxybenzyl ether
2-(3-Chlorophenyl)-3,3,3-trifluoropropyl 4-fluoro-3-phenoxybenzyl ether
2-(5-Indanyl)-3,3,3-trifluoropropyl 4-fluoro-3-phenoxybenzyl ether
2-(5-Indanyl)-3,3,3-trifluoropropyl 3-phenoxybenzyl ether
2-(4-Ethoxyphenyl)-3,3,3-trifluoropropyl 4-fluoro-3-benzylbenzyl ether
2-(3,4-Dichlorophenyl)-3,3,3-trifluoropropyl 3-phenoxybenzyl ether
2-(4-Ethoxyphenyl)-3,3,3-trifluoropropyl 3-benzylbenzyl ether
2-(4-Chlorophenyl)-3,3,3-trifluoropropyl 4-fluoro-3-benzylbenzyl ether
2-(2-Bromophenyl)-3,3,3-trifluoropropyl 3-benzylbenzyl ether
2-(4-Ethoxyphenyl)-3,3,3-trifluoropropyl 4-fluoro-3-(4-bromobenzyl)benzyl ether
2-(4-Ethoxyphenyl)-3,3,3-trifluoropropyl 4-fluoro-3-phenylthiobenzyl ether
2-(4-Ethoxyphenyl)-3,3,3-trifluoropropyl 3-phenylthiobenzyl ether
2-(4-Ethoxyphenyl)-3,3,3-trifluoropropyl 4-fluoro-3-(4bromophenylthio)benzyl ether
2-(4-Chlorophenyl)-3,3,3-trifluoropropyl 4-fluoro-3-phenylthiobenzyl ether
2-(4-Ethoxyphenyl)-3,3,3-trifluoropropyl 4-fluoro-3-trifluoromethylphenoxy)benzyl ether
2-(4-Ethoxyphenyl)-3,3,3-trifluoropropyl 3-(4-trifluoromethylphenoxy)benzyl ether
2-(4-Chlorophenyl)-3,3,3-trifluoropropyl 4-fluoro-3-(4-trifluoromethylphenoxy)benzyl ether
2-(4-Ethoxyphenyl)-3,3,3-trifluoropropyl 4-fluoro-3-(4-trifluoromethoxyphenoxy)benzyl ether
2-(4-Ethoxyphenyl)-3,3,3-trifluoropropyl 3-(4-trifluoromethoxyphenoxy)benzyl ether
2-(4-Ethoxyphenyl)-3,3,3-trifluoropropyl 4-fluoro-3-(4-difluoromethoxyphenoxy)benzyl ether
2-(4-Ethoxyphenyl)-3,3,3-trifluoropropyl 3-(4-difluoromethoxyphenoxy)benzyl ether
2-(4-Ethoxyphenyl)-3,3,3-trifluoropropyl 4-fluoro-3-(4-methoxyphenoxy)benzyl ether
2-(4-Ethoxyphenyl)-3,3,3-trifluoropropyl 3-(4-methoxyphenoxy)benzyl ether
2-(Tetralin-6-yl)-3,3,3-trifluoropropyl 4-fluoro-3-phenoxybenzyl ether
2-(2-Methy-2,3-dihydrobenzofuran-5-yl)-3,3,3-trifluoropropyl 4-fluoro-3-phenoxybenzyl ether
2-(2,2-Dimethyl-2,3-dihydrobenzofuran-5-yl)-3,3,3-trifluoropropyl 4-fluoro-3-phenoxybenzyl ether
2-(2,3-Dihydrobenzofuran-5-yl)-3,3,3-trifluoropropyl 4-fluoro-3-phenoxybenzyl ether
2-(3-Chloro-4-trifluoromethylphenyl)-3,3,3-trifluoropropyl 4-fluoro-3-phenoxybenzyl ether Examples of the alcohol compound represented by the formula (III) will be given below:
2-(4-Ethoxyphenyl)-3,3,3-trifluoropropanol
2-(4-Methoxyphenyl)-3,3,3-trifluoropropanol
2-(4-i-Propoxyphenyl)-3,3,3-trifluoropropanol
2-(4-n-Propoxyphenyl)-3,3,3-trifluoropropanol
2-(4-Difluoromethoxyphenyl)-3,3,3-trifluoropropanol
2-(4-Trifluoromethoxyphenyl)-3,3,3-trifluoropropanol
2-(4-(1,1,2,2-Tetrafluoroethoxy)phenyl)-3,3,3-trifluoropropanol
2-(4-(1,1,2-Trifluoro-2-chloroethoxy)phenyl)-3,3,3-trifluoropropanol
2-(4-Methylphenyl)-3,3,3-trifluoropropanol
2-(4-Ethylphenyl)-3,3,3-trifluoropropanol
2-(4-i-Propylphenyl)-3,3,3-trifluoropropanol
2-(4-n-Propylphenyl)-3,3,3-trifluoropropanol
2-(4-t-Butylphenyl)-3,3,3-trifluoropropanol
2-(3-Methylphenyl)-3,3,3-trifluoropropanol
2-(4-Trifluoromethylphenyl)-3,3,3-trifluoropropanol
2-(3-Trifluoromethylphenyl)-3,3,3-trifluoropropanol
2-(4-Pentafluoroethylphenyl)-3,3,3-trifluoropropanol
2-(4-Heptafluoropropylphenyl)-3,3,3-trifluoropropanol
2-(4-(2-Propenyloxy)phenyl)-3,3,3-trifluoropropanol
2-(4-(2-Propenyl)phenyl)-3,3,3-trifluoropropanol
2-(4-Vinylphenyl)-3,3,3-trifluoropropanol
2-(4-Chlorophenyl)-3,3,3-trifluoropropanol
2-(4-Fluorophenyl)-3,3,3-trifluoropropanol
2-(4-Bromophenyl)-3,3,3-trifluoropropanol
2-(3-Chlorophenyl)-3,3,3-trifluoropropanol
2-(3-Fluorophenyl)-3,3,3-trifluoropropanol
2-Phenyl-3,3,3-trifluoropropanol
2-(3,4-Methylenedioxyphenyl)-3,3,3-trifluoropropanol
2-(2,3-Dihydrobenzofuran-5-yl)-3,3,3-trifluoropropanol 2-(2,3-Dihydro-2methylbenzofuran-5yl)-3,3,3-trifluoropropanol
2-(2,3-Dihydro-2,2-timethylbenzofuran-5yl)-3,3,3-trifluoropropanol
2-(5-Indanyl)-3,3,3-trifluoropropanol
2-(6-Tetralinyl)-3,3,3-trifluoropropanol
2-(3,4-Dichlorophenyl)-3,3,3-trifluoropropanol
2-(3,4-Difluorophenyl)-3,3,3-trifluoropropanol
2-(3,4-Dimethylphenyl)-3,3,3-trifluoropropanol
2-(3,4-Dimethoxyphenyl)-3,3,3-trifluoropropanol
2-(3-Chloro-4-ethoxyphenyl)-3,3,3-trifluoropropanol
2-(3-Fluoro-4-ethoxyphenyl)-3,3,3-trifluoropropanol
2-(3-Chloro-4-trifluoromethylphenyl)-3,3,3-trifluoropropanol
2-(3-Methoxyphenyl)-3,3,3-trifluoropropanol The alcohol compound described above, represented by the formula (III) is a novel compound, and can be produced, for example, by reacting the aldehyde compound represented by the general formula (IV),

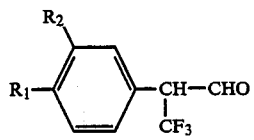

(IV)

wherein $R_1$ and $R_2$ have the same meanings as described above, with a reducing agent.

More particularly, the above alcohol compounds represented by the formula (III) can be produced by reacting the compound represented by the formula (IV) with a reducing agent (e.g. sodium borohydride, potassium borohydride, diisobutylalminum hydride) in an inert solvent (e.g. methanol, ethanol, water, tetrahydrofuran, diethyl ether, toluene, n-hexane) for 0.5 to 12 hours at a temperature from $-20°$ C. to $50°$ C.

Examples of the aldehyde compound represented by the formula (IV) will be given below:
2-(4-Ethoxyphenyl)-3,3,3-trifluoropropanol
2-(4-Methoxyphenyl)-3,3,3-trifluoropropanol
2-(4-i-Propoxyphenyl)-3,3,3-trifluoropropanol
2-(4-n-Propoxyphenyl)-3,3,3-trifluoropropanol
2-(4-Difluoromethoxyphenyl)-3,3,3-trifluoropropanol
2-(4-Trifluoromethoxyphenyl)-3,3,3-trifluoropropanol
2-(4-(1,1,2,2-Tetrafluoroethoxy)phenyl)-3,3,3-trifluoropropanol
2-(4-(1,1,2-Trifluoro-2-chloroethoxy)phenyl)-3,3,3-trifluoropropanol
2-(4-Methylphenyl)-3,3,3-trifluoropropanol
2-(4-Ethylphenyl)-3,3,3-trifluoropropanol
2-(4-i-propylphenyl)-3,3,3-trifluoropropanol
2-(4-n-Propylphenyl)-3,3,3-trifluoropropanol
2-(4-t-Butylphenyl)-3,3,3-trifluoropropanol
2-(3-Methylphenyl)-3,3,3-trifluoropropanol
2-(4-Trifluoromethylphenyl)-3,3,3-trifluoropropanol
2-(3-Trifluoromethylphenyl)-3,3,3-trifluoropropanol
2-(4-Pentafluoroethylphenyl)-3,3,3-trifluoropropanol
2-(4-Heptafluoropropylphenyl)-3,3,3-trifluoropropanol
2-(4-(2-Propenyloxy)phenyl)-3,3,3-trifluoropropanol
2-(4-(2-Propenyl)phenyl)-3,3,3-trifluoropropanol
2-(4-Vinylphenyl)-3,3,3-trifluoropropanol
2-(4-Chlorophenyl)-3,3,3-trifluoropropanol
2-(4-Fluorophenyl)-3,3,3-trifluoropropanol
2-(4-Bromophenyl)-3,3,3-trifluoropropanol
2-(3-Chlorophenyl)-3,3,3-trifluoropropanol
2-(3-Fluorophenyl)-3,3,3-trifluoropropanol
2-Phenyl-3,3,3-trifluoropropanol
2-(3,4-Methylenedioxyphenyl)-3,3,3-trifluoropropanol
2-(2,3-Dihydrobenzofuran-5-yl)-3,3,3-trifluoropropanol
2-(2,3-Dihydro-2-methylbenzofuran-5yl)-3,3,3-trifluoropropanol
2-(2,3-Dihydro-2,2-dimethylbenzofuran-5-yl)-3,3,3-trifluoropropanol
2-(5-Indanyl)-3,3,3-trifluoropropanol
2-(6Tetralinyl)-3,3,3-trifluoropropanol
2-(3,4-Dichlorophenyl)-3,3,3-trifluoropropanol
2-(3,4-Difluorophenyl)-3,3,3-trifluoropropanol
2-(3,4-Dimethylphenyl)-3,3,3-trifluoropropanol
2-(3,4-Dimethoxyphenyl)-3,3,3-trifluoropropanol
2-(3-Chloro-4-ethoxyphenyl)-3,3,3-trifluoropropanol
2-(3-Fluoro-4-ethoxyphenyl)-3,3,3-trifluoropropanol
2-(3-Chloro-4-trifluoromethylphenyl)-3,3,3-trifluoropropanol
2-(3-Methoxyphenyl)-3,3,3-trifluoropropanol The aldehyde compound described above, represented by the formula (IV) is a novel compound, and can be produced, for example, through the following scheme.

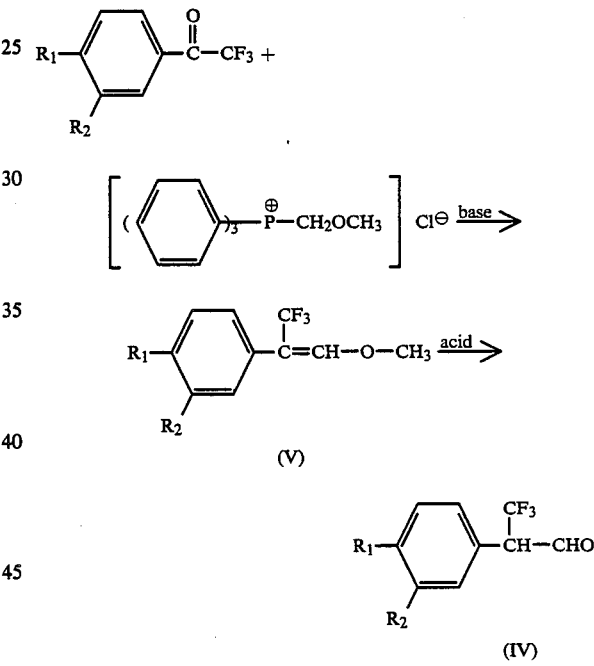

wherein $R_1$ and $R_2$ have the same meanings as described above. Namely, the preparation of the aldehyde represented by the formula (IV) shown by the above-mentioned scheme will be explained in detail below:

1 3,3,3-trifluoro-2-phenylpropenyl ether compound represented by the formula (V) can be produced by reacting the α,α,α-trilfuoroacetophenone derivatives with methoxymethylenetriphenylphosphorane, which can be obtained be reacting methoxymethyltriphenylphosphonium chloride with a base (e.g. n-butyllithium, methyllithium, phenyllithium, potassium t-butoxide, sodium ethoxide) in an inert solvent (e.g. diethyl ether, THF, ethyleneglycol dimethyl ether, t-butanol, ethanol), for 20 minutes to 6 hours at a temperature from $-50°$ C. to $30°$ C. under an inert gas atmosphere. 2 The aldehyde compound represented by the formula (IV) can be produced by reacting the compound represented by the formula (V) with an acid (e.g. perchloric acid, hydrochloric acid, sulfuric acid) in an inert solvent (e.g.

diethyl ether, tetrahydrofuran, dioxane, ethyleneglycol dimethyl ether, dichloromethane, dichloroethane, n-hexane, benzene, toluene, water) for 1 to 72 hours from 0° C. to heating condition.

Also, the aldehyde compound represented by the general formula (IV)' can be produced through the following scheme:

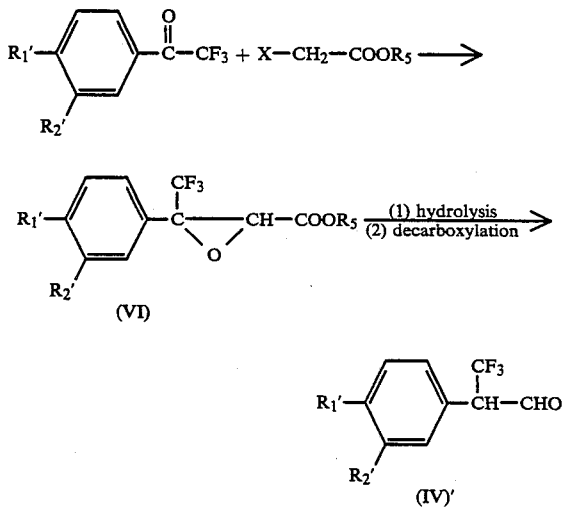

wherein $R_1'$ and $R_2'$, which may be identical or different, represent a hydrogen atom or an alkyl (e.g. $C_{1-5}$ lower alkyl) or alkoxyl (e.g. $C_{1-5}$ lower alkoxyl) group, or represent, taken together, methylenedioxy, alkylene (e.g. $C_{3-4}$ lower alkylene), ethylenoxy or alkylethoxylenoxy (e.g. ethylenoxy substituted with $C_{1-5}$ lower alkyl) group, and X have the same meanings as described above, and $R_5$ represents an alkyl (e.g. $C_{1-6}$ lower alkyl) group. Namely, the preparation of the aldehyde represented by the formula (IV)' shown by the above-mentioned will be also explained in detail below:

1' 2,3-Epoxy-4,4,4-trifluorobutyrate represented by the formula (VI) can be produced by reacting the α,α,α-trifluoroacetophenone derivative with a haloacetate (e.g. methyl chloroacetate, ethyl chloroacetate, methyl bromoacetate, ethyl bromoacetate) in the presence of a base (e.g. potassium t-butoxide, potassium t-amyloxide, sodium ethoxide, sodium methoxide) in an inert solvent (e.g. t-butyl alcohol, t-amyl alcohol, ethanol, methanol, 1,2-dimethoxyethane) for 1–24 hours from 0° C. to the refluxing temperature of the solvent used.

2' The aldehyde compound represented by the formula (IV)' can be produced by the hydrolysis of the compound represented by the formula (VI) and subsequent decarboxylation. Namely, the compound represented by the formula (VI) is hydrolized with a base (e.g. potassium hydroxide, sodium hydroxide, potassium carbonate) in an inert solvent (e.g. water, methanol, ethanol, tetrahydrofuran) for 1 to 24 hours at a temperature from 0° C. to 50° C. and followed by heating to 100°–200° C.

Examples of the aldehyde compound represented by the formula (IV)' will be given below:
2-(4-Ethoxyphenyl)-3,3,3-trifluoropropanol
2-(4-Methoxyphenyl)-3,3,3-trifluoropropanol
2-(4-i-Propoxyphenyl)-3,3,3-trifluoropropanol
2-(4-n-Propoxyphenyl)-3,3,3-trifluoropropanol
2-(4-Methylphenyl)-3,3,3-trifluoropropanol
2-(4-Ethylphenyl)-3,3,3-trifluoropropanol
2-(4-i-Propylphenyl)-3,3,3-trifluoropropanol
2-(4-n-Propylphenyl)-3,3,3-trifluoropropanol
2-(4-t-Butylphenyl)-3,3,3-trifluoropropanol
2-(3-Methylphenyl)-3,3,3-trifluoropropanol
2-Phenyl)-3,3,3-trifluoropropanol
2-(3,4-Methylenedioxyphenyl)-3,3,3-trifluoropropanol
2-(2,3-Dihydrobenzofuran-5-yl)-3,3,3-trifluoropropanol
2-(2,3-Dihydro-2-methylbenzofuran-5-yl)-3,3,3-trifluoropropanol
2-(2,3-Dihydro-2,2-dimethylbenzofuran-5-yl)-3,3,3-trifluoropropanol
2-(5-Indanyl)-3,3,3-trifluoropropanol
2-(6-Tetralinyl)-3,3,3-trifluoropropanol
2-(3,4 -Dimethylphenyl)-3,3,3-trifluoropropanol
2-(3,4 -Dimethoxyphenyl)-3,3,3-trifluoropropanol
2-(3-Methoxyphenyl)-3,3,3-trifluoropropanol The followings show the synthetic examples of the ether compound of the present invention.

EXAMPLE 1

Synthesis of 2-(4-ethoxyphenyl)-3,3,3-trifluoropropyl 3-phenoxybenzyl ether (compound (1))

Under a nitrogen atmosphere, 132 mg of sodium hydride (60% oil dispersion) was added to 20 ml of dry DMF. A solution of 0.77 g of 2-(4-ethoxyphenyl)-3,3,3-triflouropropanol and 0.69 g of 3-phenoxybenzyl bromide in 5 ml of dry DMF was then added at room temperature, and the reaction solution was stirred at that temperature for 14 hours. Thereafter, the reaction mixture was poured into dilute HCl-ice water and extracted twice with diethyl ether. The ether layers were combined, washed with saturated sodium chloride solution and dried over anhydrous magnesium sulfate. The solvent was removed under a reduced pressure, and the residue was subjected to column chromatography on silica gel [eluted with n-hexane/ethyl acetate (25:1 ) mixture] to obtain 0.61 g of the desired compound.
$n_D^{21.5}$ 1.5447.

$^1$H-NMR (in CDCl$_3$, TMS as an internal standard).
δ (ppm) 1.38 (t, 3H), 3.20–4.20 (m, 3H), 4.00 (q, 2H), 4.45 (s, 2H), 6.60–7.50 (m, 13H).

$^{19}$F-NMR (in CDCl$_3$, CF$_3$COOH as an external standard).
δ (ppm) +12.2 (d, J=10 Hz).

EXAMPLE 2

Synthesis of 2-(4-ethoxyphenyl)-3,3,3-trifluoropropyl 4-fluoro-3-phenoxybenzyl ether (compound (2))

Under a nitrogen atmosphere, 113 mg of sodium hydride (60% oil dispersion) was added to 20 ml of dry DMF. A solution of 0.60 g of 2-(4-ethoxyphenyl)-3,3,3-trifluoropropanol and 0.65 g of 4-fluoro-3-phenoxybenzyl bromide in 5 ml of dry DMF was then added at room temperature, and the reaction solution was stirred at that temperature for 15 hours. Thereafter, the reaction mixture was poured into dilute HCl-ice water and extracted twice with diethyl ether. The ether layers were combined, washed with saturated sodium chloride solution and dried over anhydrous magnesium sulfate. The solvent was removed under a reduced pressure, and the residue was subjected to column chromatography on silica gel [eluted with n-hexane/ethyl acetate (25:1) mixture] to obtain 0.64 g of the desired compound.
$n_D^{22.5}$ 1.5352.

¹H-NMR (in CDCl₃, TMS as an internal standard).

δ (ppm) 1.38 (t, 3H), 3.15–4.20 (m, 3H), 3.97 (q, 2H), 4.36 (s, 2H), 6.68–7.50 (m, 12H).

¹⁹F-NMR (in CDCl₃, CF₃COOH as an external standard).

δ (ppm) +13.5 (d, 3F, J=9 Hz) −52.2 (b, 1F).

EXAMPLE 3

Synthesis of 2-(3,4 methylenedioxyphenyl)-3,3,3trifluoropropyl 3-phenoxybenzyl ether (compound (6))

Under a nitrogen atmosphere, 0.18 g of sodium hydride (60% oil dispersion) was added to 20 ml of dry THF. A solution of 1.0 g of 2-(3,4-methylenedioxyphenyl)-3,3,3-trifluoropropanol and 1.17 g of 3-phenoxybenzyl bromide in 10 ml of dry THF was then added with ice-cooling, and the reaction solution was stirred at room temperature for 14 hours. Thereafter, the reaction mixture was poured into dilute HCl-ice water and extracted twice with diethyl ether. The ether layers were combined, washed with water and dried over anhydrous magnesium sulfate. The solvent was removed under a reduced pressure, and the residue was subjected to column chromatography on silica gel [eluted with n-hexane/ethyl acetate (25:1) mixture] to obtain 1.2 g of the desired compound.

$n_D^{22.5}$ 1.5531.

¹H-NMR (in CDCl₃, TMS as an internal standard).

δ (ppm) 3.25–4.15 (m, 3H), 4.42 (s, 2H), 5.88 (s, 2H), 6.60–7.50 (m, 12H).

¹⁹F-NMR (in CDCl₃, CF₃COOH as an external standard).

δ (ppm) +11.6 (d, J=9.5 Hz).

EXAMPLE 4

Synthesis of 2-(4-methoxyphenyl)-3,3,3-trifluoropropyl-3-phenoxybenzyl ether (compound (19))

Under a nitrogen atmosphere, 0.54 g of sodium hydride (60% oil dispersion) was added to 30 ml of dry THF. A solution of 2.97 g of 2-(4-methoxyphenyl)-3,3,3-trifluoropropanol and 3.53 g of 3-phenoxybenzyl bromide in 20 ml of dry THF was then added with ice-cooling and the reaction solution was stirred at room temperature for 14 hours. Thereafter, the reaction mixture was poured into dilute HCl-ice water and extracted twice with diethyl ether. The ether layers were combined, washed with water and dried over anhydrous magnesium sulfate. The solvent was removed under a reduced pressure, and the residue was subjected to column chromatography on silica gel [eluted with n-hexane/ethyl acetate (25:1) mixture] to obtain 2.6 g of the desired compound.

$n_D^{26.0}$ 1.5452.

¹H-NMR (in CDCl₃, TMS as an internal standard).

δ (ppm) 3.20–4.20 (m, 3H), 3.63 (s, 3H), 4.32 (s, 2H), 6.60–7.30 (m, 13H).

¹⁹F-NMR (in CDCl₃, CF₃COOH as an external standard).

δ (ppm) +12.7 (d, J=9.6 Hz).

EXAMPLE 5

Synthesis of 2-(4-chlorophenyl-3,3,3-trifluoropropyl 4-fluoro-3phenoxybenzyl ether (compound (4))

Under a nitrogen atmosphere, 64 mg of sodium hydride (60% oil dispersion) was added to 10 ml of dry THF. A solution of 0.40 g of 2-(4-chlorophenyl)-3,3,3-trifluoropropanol and 0.40 g of 4-fluoro-3-phenoxybenzyl bromide in 10 ml of dry THF was then added with ice-cooling, and the reaction solution was stirred with ice-cooling for 2 hours and at room temperature for 14 hours. Thereafter, the reaction mixture was poured into dilute HCl-ice water and extracted twice with diethyl ether. The ether layers were combined, washed with saturated sodium chloride solution and dried over anhydrous magnesium sulfate. The solvent was removed under a reduced pressure, and the residue was subjected to column chromatography on silica gel [eluted with n-hexane/ethyl acetate (50:1) mixture] to obtain 144 mg of the desired compound.

$n_D^{25.5}$ 1.5372.

¹H-NMR (in CDCl₃, TMS as an internal standard).

δ (ppm) 3.30–4.15 (m, 3H), 4.40 (s, 2H), 6.08–7.60 (m, 12H).

¹⁹F-NMR (in CDCl₃, CF₃COOH as an external standard).

δ (ppm) +14.5 (d, 3F, J=9 Hz) −51.2 (m, 1F).

EXAMPLE 6

Synthesis of 2-(4-chlorophenyl)3,3,3-trifluoropropyl 3-phenoxybenzyl ether (compound (3))

Under a nitrogen atmosphere, 135 mg of sodium hydride (60% oil dispersion) was added to 20 ml of dry THF. A solution of 0.30 g or 2-(4-chlorophenyl)3,3,3-trifluoropropanol and 0.34 g of 3-phenoxybenzyl bromide in 20 ml of dry THF was then added with ice-cooling, and the reaction solution was stirred with ice-cooling for 1 hour and at room temperature for 12 hours. Thereafter, the reaction mixture was poured into dilute HCl-ice water and extracted twice with diethyl ether. The ether layers were combined, washed with saturated sodium chloride solution and dried over anhydrous magnesium sulfate. The solvent was removed under a reduced pressure, and the residue was subjected to column chromatography on silica gel [eluted with n-hexane/toluene (2:1) mixture] to obtain 250 mg of the desired compound.

$n_D^{23.0}$ 1.5512.

¹H-NMR (in CDCl₃, TMS as an internal standard).

δ (ppm) 3.30–4.15 (m, 3H), 4.48 (s, 2H), 6.80–7.60 (m, 13H).

¹⁹F-NMR (in CDCl₃, CF₃COOH as an external standard).

δ (ppm) +13.8 (d, J=10 Hz).

EXAMPLE 7

Synthesis of 2-(4-ethylphenyl)-3,3,3-trifluoropropyl 3phenoxybenzyl ether (compound (7))

Under a nitrogen atmosphere, 165 mg of sodium hydride (60% oil dispersion) was added to 20 ml of dry THF. A solution of 1.0 g of 2-(4-ethylphenyl)-3,3,3-trifluoropropanbol and 0.84 g of 3-phenoxybenzyl bromide in 20 ml of dry THF was then added with ice-cooling, and the reaction solution was stirred with ice-cooling for 1 hour and at room temperature for 12 hours. Thereafter, the reaction mixture was poured into dilute HCl-ice water and extracted twice with diethyl ether. The ether layers were combined, washed with saturated sodium chloride solution and dried over anhydrous magnesium sulfate. The solvent was removed under a reduced pressure, and the residue was subjected to column chromatography on silica gel [eluted with n-hexane/toluene (2:1) mixture] to obtain 0.97 g of the desired compound).

$n_D^{22.5}$ 1.5402.

$^1$H-NMR (in CDCl$_3$, TMS as an internal standard).

δ (ppm) 1.25 (t, 3H), 2.68 (q, 2H), 3.30–4.18 (m, 3H), 4.50 (s, 2H), 6.80–7.56 (m, 13H).

$^{19}$F-NMR (in CDCl$_3$, CF$_3$COOH as an external standard).

δ (ppm) +13.2 (d, J=9.5 Hz).

EXAMPLE 8

Synthesis of 2-(3-chloro-4-ethoxyphenyl)-3,3,3-trifluoropropyl 3-phenoxybenzyl ether (compound (34))

Under a nitrogen atmosphere, 45 mg of sodium hydride (60% oil dispersion) was added to 10 ml of dry THF. A solution of 300 mg of 2-(3-chloro-4-ethoxyphenyl)-3,3,3-trifluoropropanol and 264 mg of 3-phenoxybenzyl bromide in 15 ml of dry THF was the added with ice-cooling, and the reaction solution was stirred with ice-cooling for 2 hours and at room temperature for 14 hours. Thereafter, the reaction mixture was poured into dilute HCl-ice water and extracted twice with diethyl ether. The ether layers were combined, washed with saturated sodium chloride solution and dried over anhydrous magnesium sulfate. The solvent was removed under a reduced pressure, and the residue was subjected to column chromatography on silica gel [eluted with n-hexane/toluene (2:1) mixture] to obtain 164 mg of the desired mixture.

$n_D^{23.5}$ 1.5467.

$^1$H-NMR (in CDCl$_3$, TMS as an internal standard).

δ (ppm) 1.46 (t, 3H), 3.20–4.20 (m, 3H), 4.08 (q, 2H), 4.47 (s, 2H), 6.70–7.55 (m, 12H).

$^{19}$F-NMR (in CDCl$_3$, CF$_3$COOH as an external standard).

δ (ppm) 12.5 (d, J=10 Hz).

EXAMPLE 9

Synthesis of 2-(4-ethoxyphenyl)-3,3,3-trifluoropropyl 3-(4-fluorophenoxy)benzyl ether (compound (11))

Under a nitrogen atmosphere, 171 mg of sodium hydride (60% oil dispersion) was added to 15 ml of dry DMF. A solution of 1.0 g of 2-(4-ethoxyphenyl)-3,3,3-trifluoropropanol and 1.08 g of 3-(4-fluorophenoxy)benzyl bromide in 20 ml of dry DMF was then added with ice-cooling, and the reaction solution was stirred with ice-cooling for 1 hour and at room temperature for 12 hours. Thereafter, the reaction mixture was poured into dilute HCl-ice water and extracted twice with diethyl ether. The ether layers were combined, washed with saturated sodium chloride solution and dried over anhydrous magnesium sulfate. The solvent was removed under a reduced pressure, and the residue was subjected to column chromatography on silica gel [eluted with n-hexane/ethyl acetate (25:1) mixture] to obtain 1.30 g of the desired compound.

$n_D^{23.0}$ 1.5335.

$^1$H-NMR (in CDCl$_3$, TMS as an internal standard).

δ (ppm) 1.36 (t, 3H), 3.20–4.20 (m, 3H), 3.98 (q, 2H), 4.40 (s, 2H), 6.66–7.40 (m, 12H).

$^{19}$F-NMR (in CDCl$_3$, CF$_3$COOH as an external standard).

δ (ppm) +13.8 (d, 3F, J=9 Hz) −38.6 (m, 1F).

EXAMPLE 10

Synthesis of 2-(4-ethoxyphenyl)-3,3,3-trifluoropropyl 6-phenoxypyridin-2-ylmethyl ether compound (9))

Under a nitrogen atmosphere, 82 mg of sodium hydride (60% oil dispersion) was added to 15 ml of dry DMF. A solution of 0.4 g of 2-(4-ethoxyphenyl)-3,3,3-trifluoropropanol and 338 mg of 6-phenoxy-2-chloromethylpyridine in 20 ml of dry DMF was then added with ice-cooling, and the reaction solution was stirred with ice-cooling for 1 hour and at room temperature for 12 hours. Thereafter, the reaction mixture was poured into dilute HCl-ice water and extracted twice with diethyl ether. The ether layers were combined, washed with saturated sodium chloride solution and dried over anhydrous magnesium sulfate. The solvent was removed under a reduced pressure, and the residue was subjected to column chromatography on silica gel [eluted with n-hexane/ethyl acetate (25:1) mixture] to obtain 120 mg of the desired compound.

$n_D^{23.5}$ 1.5372.

$^1$H-NMR (in CDCl$_3$, TMS as an internal standard).

δ (ppm) 1.40 (t, 3H), 3.25–4.20 (m, 3H), 4.20 (q, 2H), 4.48 (s, 2H), 6.60–7.72 (m, 12H).

$^{19}$F-NMR (in CDCl$_3$, CF$_3$COOH as an external standard).

δ (ppm) +13.0 (d, J=9 Hz).

EXAMPLE 11

Synthesis of 2-(4-ethoxyphenyl)-3,3,3-trifluoropropyl 3-(4-chlorophenoxy)benzyl ether (compound (12))

Under a nitrogen atmosphere, 171 mg of sodium hydride (60% oil dispersion) was added to 20 ml of dry THF. A solution of 1.0 g of 2-(4-ethoxyphenyl)-3,3,3-trifluoropropanol and 1.25 g of 3-(4-chlorophenoxy)benzyl bromide in 30 ml of dry THF was then added with ice-cooling, and the reaction solution was stirred with ice-cooling for 1 hour and at room temperature for 12 hours. Thereafter, the reaction mixture was poured into dilute HCl-ice water and extracted twice with diethyl ether. The ether layers were combined, washed with saturated sodium chloride solution and dried over anhydrous magnesium sulfate. The solvent was removed under a reduced pressure, and the residue was subjected to column chromatography on silica gel [eluted with n-hexane/ethyl acetate (50:1) mixture] to obtain 1.22 of the desired compound.

$n_D^{24.0}$ 1.5483.

$^1$H-NMR (in CDCl$_3$, TMS as an internal standard).

δ (ppm) 1.38 (t, 3H), 3.20–4.08 (m, 3H), 3.90 (q, 2H), 4.35 (s, 2H), 6.58–7.30 (m, 12H).

$^{19}$F-NMR (in CDCl$_3$, CF$_3$COOH as an external standard).

δ (ppm) +13.3 (d, J=10 Hz).

EXAMPLE 12

Synthesis of 2-(4-ethoxyphenyl)-3,3,3-trifluoropropyl 3-(4-bromophenoxy)benzyl ether (compound (13))

Under a nitrogen atmosphere, 171 mg of sodium hydride (60% oil dispersion) was added to 20 ml of dry THF. A solution of 1.0 g of 2-(4-ethoxyphenyl)-3,3,3-trifluoropropanol and 1.30 g of 3-(4-bromophenoxy)benzyl bromide in 30 ml of dry THF was then added with ice-cooling, and the reaction solution was stirred with ice-cooling for 1 hour and at room temperature for 12 hours. Thereafter, the reaction mixture was poured into dilute HCl-ice water and extracted twice with diethyl ether. The ether layers were combined, washed with saturated sodium chloride solution and dried over anhydrous magnesium sulfate. The solvent was removed under a reduced pressure, and the residue was subjected to column chromatography on silica gel [eluted with n-hexane/ethyl acetate (50:1) mixture] to obtain 0.58 g of the desired compound.

$n_D^{22.5}$ 1.5579.

$^1$H-NMR (in CDCl$_3$, TMS as an internal standard).

δ (ppm) 1.40 (t, 3H), 3.20–4.20 (m, 3H), 4.02 (q, 2H), 4.48 (s, 2H), 6.70–7.56 (m, 12H).

$^{19}$F-NMR (in CDCl$_3$, CF$_3$COOH as an external standard).

δ (ppm) +12.6 (d, J=10 Hz).

EXAMPLE 13

Synthesis of 2-(4-fluorophenyl)-3,3,3-trifluoropropyl 3phenylbenzyl ether (compound (5))

Under a nitrogen atmosphere, 0.50 g of 2-(4-fluorophenyl)-3,3,3-trifluoropropanol and 0.63 g of 3-phenoxybenzyl bromide was dissolved in 15 ml of dry diethyleneglycol dimethylether. Into the solution, 1.83 g of dry cesium fluoride was added at room temperature, and the reaction solution was stirred at room temperature for 48 hours. Thereafter, the reaction solution was poured into dilute HCl-ice water and extracted twice with diethyl ether. The ether layers were combined, washed with saturated sodium chloride solution and dried over anhydrous magnesium sulfate. The solvent was removed under a reduced pressure, and the residue was subjected to preparative thin-layer chromatography on silica gel to obtain αmg of the desired compound.

$n_D^{24.0}$ 1.5348.

$^1$H-NMR (in CDCl$_3$, TMS as an internal standard).

δ (ppm) 3.25–4.12 (m, 3H), 4.48 (s, 2H), 6.78–7.50 (m, 13H).

$^{19}$F-NMR (in CDCl$_3$, CF$_3$COOH as an external standard).

δ (ppm) +11.2 (d, 3F, J=10 Hz).

EXAMPLE 14

Synthesis of 2-(3-chloro-4-ethoxyphenyl)-3,3,3-trifluoropropyl 3-(4-fluorophenoxy)benzyl ether (Compound (20))

Under a nitrogen atmosphere, 60 mg of sodium hydride (60% oil dispersion) was added to 10 ml of dry THF. A solution of 0.41 g of 2-(3-chloro-4-ethoxyphenyl)-3,3,3-trifluoropropanol and 1.43 g of 3-(4-fluorophenoxy)benzyl bromide in 10 ml of dry THF was then added with ice-cooling, and the reaction solution was stirred with ice-cooling for 1 hour and at room temperature for 12 hours. Thereafter, the reaction mixture was poured into dilute HCl-ice water and extracted twice with diethyl ether. The ether layers were combined, washed with saturated sodium chloride solution and dried over anhydrous magnesium sulfate. The solvent was removed under a reduced pressure, and the residue was subjected to column chromatography on silica gel [eluted with n-hexane/ethyl acetate (40:1) mixture] to obtain 255 mg of the desired compound.

$n_D^{23.0}$ 1.5401.

$^1$H-NMR (in CDC$_3$, TMS as an internal standard).

δ (ppm) 1.46 (t, 3H), 3.30–4.22 (m, 3H), 4.02 (q, 2H), 4.45 (s, 2H), 6.80–7.51 (m, 11H).

$^{19}$F-NMR (in CDCl$_3$, CF$_3$COOH as an external standard).

δ (ppm) +11.3 (d, 3F, J=10 Hz) −40.5 (m, 1F).

EXAMPLE 15

Synthesis of 2-(4-ethoxyphenyl)-3,3,3-trifluoropropyl 4-fluoro-3-anilinobenzyl ether (compound (10))

Under a nitrogen atmosphere, 120 mg of sodium hydride (60% oil dispersion) was added to 10 ml of dry THF. A solution of 0.69 of 2-(4-ethoxyphenyl)-3,3,3-trifluoropropanol and 0.82 g or 4-fluoro-3-anilinobenzyl bromide in 20 ml of dry THF was then added with ice-cooling, and the reaction solution was stirred with ice-cooling for 1 hour and at room temperature for 46 hours. Thereafter, the reaction mixture was poured into ice water and adjusted to pH 6 with dilute HCl and extracted twice with diethyl ether. The ether layers were combined, washed with saturated sodium chloride solution and dried over anhydrous magnesium sulfate. The solvent was removed under a reduced pressure, and the residue was subjected to column chromatography on silica gel [eluted with n-hexane/ethyl acetate (25:1) mixture] to obtain 368 mg of the desired compound.

$n_D^{24.5}$ 1.5600.

$^1$H-NMR (in CDCl$_3$, TMS as an internal standard).

δ (ppm) 1.40 (t, 3H), 3.20–4.18 (m, 3H), 3.98 (q, 2H), 5.60–6.00 (b, 1H), 6.55–7.40 (m, 12H).

$^{19}$F-NMR (in CDCl$_3$, CF$_3$COOH as an external standard).

δ (ppm) +12.8 (d, J=10 Hz).

EXAMPLE 16

Synthesis of 2-(4-ethoxyphenyl-3,3,3-trifluoropropyl 3-phenoxybenzyl ether (compound (1))

Under a nitrogen atmosphere, a solution of 1.00 g of 2-(4-ethoxyphenyl)-3,3,3-trifluoropropanol in 5 ml of toluene was slowly added to the mixture of 1.12 g of 3-phenoxybenzyl bromide, 100 mg of tetrabutylammonium bromide, 1.9 g of 45% aqueous sodium hydroxide solution and 5 ml of toluene with ice-cooling. The reaction solution was stirred with ice-cooling for 3 hours and at room temperature for 12 hours. Thereafter, the reaction solution was poured into dilute HCl-ice water and extracted with toluene. The toluene layer was washed with water and dried over anhydrous magnesium sulfate. The solvent was removed under a reduced pressure, and the residue was subjected to column chromatography on silica gel [eluted with n-hexane/ethylacetate (50:1) mixture] to obtain 1.65 g of the desired compound.

$^1$H-NMR (in CDCl$_3$, TMS as an internal standard).

δ (ppm) 1.40 (t, 3H), 3.20–4.22 (m, 5H), 4.51 (s, 2H), 6.80–7.62 (m, 13H).

EXAMPLE 17

Synthesis of 2-(4-chlorophenyl)-3,3,3-trifluoropropyl 3-phenoxybenzyl ether (compound (3))

Under a nitrogen atmosphere, a solution of 12.58 g of 3-phenoxybenzyl bromide and 10.74 g of 2-(4-chlorophenyl)3,3,3-trifluoropropanol in 30 ml of toluene was slowly added to the mixture of 1.00 g of benzyltriethylammonium chloride, 12.76 g of 45% aqueous sodium hydroxide solution and 15 ml of toluene with ice-cooling. The reaction solution was stirred at room temperature for 14 hours. Thereafter, the reaction solution was poured into dilute hydrochloric acid-ice water and extracted with toluene. The toluene layer was washed with water and dried over anhydrous magnesium sulfate. The solvent was removed under a reduced pressure, and the residue was subjected to column chromatography on silica gel [eluted with n-hexane/toluene (2:1) mixture] to obtain 16.06 g of the desired compound.

$n_D^{20.0}$ 1.5528.

$^1$H-NMR (in CDCL$_3$, TMS as an internal standard).

δ (ppm) 3.25–4.15 (m, 3H), 4.44 (s, 2H), 6.78–7.60 (m, 13H).

$^{19}$F-NMR (in CDCl$_3$, CF$_3$COOH as an external standard).

δ (ppm) +12.0 (d, J=10 Hz).

EXAMPLE 18

Preparation of optically active 2-(4-ethoxyphenyl)-3,3,3-trifluoropropyl 3phenoxybenxyl ether A solution of 0.5 g of racemic 2-(4-ethoxyphenyl)-3,3,3-trifluoropropyl 3-phenoxybenzyl ether (compound (1)) in 2 ml of n-hexane was charged to an optically active HPLC column in eleven portions. Eluent fractions correspond to each enantiomer were separately collected. The combined fractions from the former eluents gave 6.5 mg of (1)-A after removal of the solvent. The latter fractions gave 6.7 mg of (1)-B after removal of the solvent.

[Separation condition]
apparatus: Liquid chromatograph LC-3A (Simadzu)
optically active column: SUMIPAX ® OA-2000
  8 mmφ × 25 cm (2 columns in tandem)
  (SUMIKA Chemical Analysis Service Ltd.)
eluent: n-hexane/ethyl acetate (500:1)
  3.5 ml/min
injection: 20 μl × 11 times

[Optical rotations and optical purities]
apparatus: Polarimeter Model 241
  (Perkin-Elmer)
(1)-A  $[\alpha]_{436}^{24}$ +28.6 (c = 0.325, n-hexane)
(1)-B  $[\alpha]_{436}^{24}$ −5.7 (c = 0.335, n-hexane)

The optical purities were given below:

(1)-A  100% e.e.*
(1)-B  64% e.e.*

*determined by HPLC analysis on the same optically active column used for preparative separation Examples of the present compound produced by the above will be shown in Table 1, but this invention is not limited to these examples only.

TABLE 1

| Compound No. | R$_1$ | R$_2$ | R$_3$ | Y | Z | R$_4$ | Refractive index (°C.) |
|---|---|---|---|---|---|---|---|
| (1) | OCH$_2$CH$_3$ | H | H | O | —CH= | H | 1.5447 (21.5) |
| (2) | " | " | F | " | " | " | 1.5352 (22.0) |
| (3) | Cl | " | H | " | " | " | 1.5512 (23.0) |
| (4) | " | " | F | " | " | " | 1.5372 (25.5) |
| (5) | F | " | H | " | " | " | 1.5348 (24.0) |
| (6) | —O—CH$_2$—O— | | " | " | " | " | 1.5531 (25.5) |
| (7) | CH$_2$CH$_3$ | H | " | " | " | " | 1.5402 (22.5) |
| (8) | CF$_3$ | H | H | O | —CH= | H | 1.5246 (27.0) |
| (9) | OCH$_2$CH$_3$ | " | " | " | N | " | 1.5372 (23.5) |
| (10) | " | " | F | NH | —CH= | " | 1.5600 (24.5) |
| (11) | " | " | H | O | " | 4-F | 1.5335 (23.0) |
| (12) | " | " | " | " | " | 4-Cl | 1.5483 (24.0) |
| (13) | " | " | " | " | " | 4-Br | 1.5579 (22.5) |
| (14) | " | " | F | " | N | H | 1.5292 (24.5) |
| (15) | OCHF$_2$ | " | H | " | —CH= | " | 1.5304 (23.5) |
| (16) | OCH$_2$CH=CH$_2$ | " | F | " | " | " | 1.5378 (21.5) |
| (17) | OCH$_2$CH$_3$ | Cl | " | " | " | " | 1.5348 (27.0) |
| (18) | Br | H | H | " | " | " | 1.5586 (23.0) |
| (19) | OCH$_3$ | H | H | O | —CH= | H | 1.5452 (26.0) |
| (20) | OCH$_2$CH$_3$ | Cl | " | " | " | 4-F | 1.5401 (23.0) |
| (21) | OCH(CH$_3$)$_2$ | H | F | " | " | H | 1.5449 (23.0) |
| (22) | CH$_3$ | " | H | " | " | " | 1.5411 (22.0) |
| (23) | —CH$_2$CH$_2$CH$_2$— | " | " | " | " | " | 1.5463 (24.0) |
| (24) | OCF$_3$ | H | " | " | " | " | 1.5250 (23.0) |
| (25) | CH$_2$CH=CH$_2$ | " | F | " | " | " | 1.5326 (23.0) |
| (26) | —OCH$_2$O— | " | " | " | " | " | 1.5444 (21.0) |
| (27) | OCH$_2$CH$_3$ | H | " | " | " | 4-Cl | 1.5409 (25.0) |
| (28) | Cl | Cl | H | " | " | H | 1.5574 (26.0) |
| (29) | CH$_2$CH$_2$CH$_3$ | H | F | " | " | " | 1.5338 (23.0) |
| (30) | OCH$_2$CH$_3$ | " | " | " | " | 3-CH$_3$ | 1.5356 (21.5) |
| (31) | F | H | F | O | —CH= | H | 1.5268 (24.5) |
| (32) | OCH$_2$CH$_3$ | " | " | " | " | 4-Br | 1.5505 (23.0) |
| (33) | " | " | " | " | " | 3-F, 4-F | 1.5208 (19.0) |

TABLE 1-continued

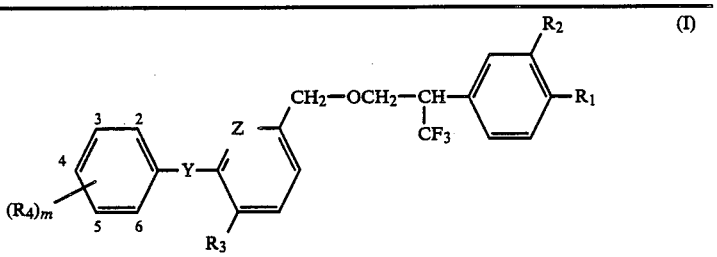

| Compound No. | Structural formula | | | | | Refractive index (°C.) |
|---|---|---|---|---|---|---|
| | R₁ | R₂ | R₃ | Y | Z | R₄ | |
| (34) | " | Cl | H | " | " | H | 1.5467 (23.5) |
| (35) | OCH₂CF₃ | H | F | " | " | " | 1.5189 (23.5) |
| (36) | Br | " | " | " | " | " | 1.5480 (19.0) |
| (37) | H | CF₃ | H | " | " | " | 1.5231 (25.0) |
| (38) | " | CH₃ | F | " | " | " | 1.5340 (21.0) |
| (39) | OCH₂CH₃ | H | H | CH₂ | " | " | 1.5405 (25.0) |
| (40) | " | " | " | S | " | " | 1.5670 (26.0) |
| (41) | " | " | " | O | " | 4-CF₃ | 1.5150 (22.0) |
| (42) | OCH₂CH₃ | H | H | O | —CH═ | 4-CH₃ | 1.5430 (21.5) |
| (43) | " | " | " | " | " | 4-OCF₃ | 1.5260 (20.0) |
| (44) | " | " | " | " | " | 4-OCF₂H | 1.5316 (21.0) |
| (45) | " | " | " | " | " | 4-OCH₃ | 1.5519 (20.0) |
| (46) | C(CH₃)₃ | " | " | " | " | H | 1.5439 (21.0) |
| (47) | —CH₂CH₂CH₂— | F | " | " | " | " | 1.5465 (19.5) |
| (48) | OCH₂CH₃ | H | H | " | " | 4-CH₂CH₃ | 1.5382 (26.0) |
| (49) | OCH₂CH═CH₂ | " | " | " | " | H | 1.5426 (25.5) |
| (50) | OCH₂CH₂CH₃ | " | " | " | " | " | 1.5432 (23.0) |
| (51) | CH₂CH₃ | " | F | " | " | " | 1.5323 (21.0) |
| (52) | —OCH(CH₃)CH₂— | H | O | —CH═ | H | 1.5676 (21.0) |
| (53) | —OC(CH₃)₂CH₂— | " | " | " | " | 1.5610 (20.0) |
| (1)-A | OCH₂CH₃ | H | " | " | " | " | * |

*Optically active isomer having an (+) optical rotation
$[\alpha]_{436}^{24}$ +28.6° (c = 0.325, n-hexane)

The followings show the synthetic examples of the alcohol represented by the formula (III), and the aldehyde represented by the formula (IV) and (IV)'.

EXAMPLE 19

Synthesis of 2-(4-ethoxyphenyl-3,3,3-trifluoropropanol (i) Synthesis of 4-ethoxy-α,α,α-trifluoroacetophenone 4-Ethoxy-α,α,α-trifluoroacetophenone was obtained from 4-ethoxybromobenzene according to the synthetic procedures for o-methoxy-α,α, α-trifluoroacetophenone described in J. Agr. Food Chem., 22, 926 (1974).
b.p. 116°–117° C. (12 mmHg).
¹H-NMR (in CDCl₃, TMS as an internal standard).
δ (ppm) 1.47 (t, 3H), 4.15 (q, 2H), 7.00(d, 2H), 8.07 (bd, 2H).

(ii) Synthesis of methyl 3-(4-ethoxyphenyl)-2,3-epoxy-4,4,4-trifluorobutyrate

Under a nitrogen atmosphere, 15.34 g of potassium t-butoxide in 200 ml of dry dimethoxyethane was added to a solution of 25.96 g of 4-ethoxy-α,α,α-trifluoroacetophenone and 14.21 g of methyl chloroacetate in 200 ml of dry dimethoxyethane with ice-cooling. The reaction solution was stirred at room temperature for 15 hours. Thereafter, the reaction mixture was poured into ice water and extracted twice with diethyl ether. The ether layers were combined, washed with saturated sodium chloride solution and dried over anhydrous magnesium sulfate. The solvent was removed under a reduced pressure and 29.55 g of the desired compound was obtained by distillation under a reduced pressure.
b.p. 113°–118° C. (0.3 mmHg).

¹H-NMR (in CDCl₃, TMS as an internal standard).
δ (ppm) 1.33 (t, 3H), 3.40 (s, 3H), 3.98 (q, 2H), 4.04 (s, 1H), 6.86 (d, 2H), 7.40 (bd, 2H).

(iii) Synthesis of 2-(4-ethoxyphenyl)-3,3,3-trifluoropropanal

Into a solution of 11.41 g of potassium hydroxide in 80 ml of ethanol and 20 ml of water, 29.55 g of methyl 3-(4-ethoxyphenyl)-2,3-epoxy-4,4,4-trifluorobutyrate was added with ice-cooling. The reaction solution was stirred at room temperature for 17 hours. Thereafter, the reaction solution was poured into ice water. The resulting solution was washed with diethyl ether and adjusted to pH 3 with 10% HCl and extracted twice with diethyl ether. The ether layers were combined and washed with saturated sodium chloride solution and dried over anhydrous magnesium sulfate. The solvent was removed under a reduced pressure and the residue was subjected to distillation under a reduced pressure by heating in an oil bath (130°–140° C.) to obtain 14.66 g of the desired aldehyde (b.p. 100°–105° C./0.3 mmHg).
¹H-NMR (in CDCl₃, TMS as an internal standard).
δ (ppm) 1.41 (t, 3H), 4.08 (q, 2H), 3.96–4.50 (m, 1H), 6.90–7.45 (m. 4H), 9.70–9.90 (m, 1H).

(iv) Synthesis of 2(4-ethoxyphenyl)-3,3,3-trifluoropropanol

A hundred milligrams of sodium borohydride was added to a solution of 1.04 g of 2-(4ethoxyphenyl)-3,3,3-trifluoropropanal in 15 ml of ethanol with ice-cooling. The reaction solution was stirred at room temperature for 4hours. Thereafter, the reaction mixture was poured into ice water and extracted twice with ethyl acetate.

The ethyl acetate layers were combined and washed with dilute HCl and saturated sodium chloride solution successively and dried over anhydrous magnesium sulfate. The solvent was removed under reduced pressure and the residue was subjected to column chromatography on silica gel [eluted with n-hexane/ethyl acetate (4:1) mixture] to obtain 0.77 g of the desired compound.

$^1$H-NMR (in CDCl$_3$, TMS as an internal standard).

δ (ppm) 1.40 (t, 3H), 1.98 (bs, 1H), 3.51–4.25 (m, 3H), 4.02 (q, 2H), 6.70–7.40 (m, 4H).

$^{19}$F-NMR (in CDCl$_3$, CF$_3$COOH as an external standard).

δ (ppm) +12.0 (bd, J=10 Hz).

EXAMPLE 20

Synthesis of 2-(4-chlorophenyl)-3,3,3-trifluoropropanol (i) Synthesis of 4-chloro-α,α,α-trifluoroacetophenone Under a nitrogen atmosphere, 110 ml of n-butyllithium/hexane solution (0.95M solution) was added to a solution of 20 g of p-bromochlorobenzene in 200 ml of dry THF at −60° C. The reaction solution was stirred at −60° C. for 1 hour and at −20° C. for 30 minutes. A solution of 17.8 g of ethyl trifluoroacetate in 20 ml of dry THF was added to the reaction solution at −60° C., followed by stirring at that temperature for 1 hour. The reaction solution was poured into dilute HCl-ice water and extracted twice with diethyl ether. The ether layers were combined and washed with saturated sodium chloride solution and dried over anhydrous magnesium sulfate. The solvent was removed under a reduced pressure and the residue was subjected to distillation under a reduced pressure to obtain 13.1 g of the desired compound.

b.p. 75° C. (14 mmHg)–82° C. (12 mmHg).

$^1$H-NMR (in CDCl$_3$, TMS as an internal standard).

δ (ppm) 7.52 (bd, 2H), 8.03 (bd, 2H).

(ii) Synthesis of 2-(4-chlorophenyl)-3,3,3-trifluoropropenyl methyl ether

Under a nitrogen atmosphere, 33.6 ml of n-butyllithium/hexane solution (1.2M solution) was added to a solution of 17.3 g of methoxymethyltriphenylphosphonium chloride in 150 ml of dry THF at −60° C. The reaction solution was stirred at −60° C. for 30 minutes and at −20° C. for 30 minutes. A solution of 7.0 g of 4-chloro-α,α,α-trifluoroacetophenone in 10 ml of dry THF was slowly added to the reaction solution at −60° C. The reaction solution was stirred at −60° C. for 1 hour and at room temperature for 12 hours. Thereafter, 200 ml of n-hexane was added to the reaction mixture and insoluble materials were filtered out. The filtrate was washed with dilute HCl-ice water and saturated sodium chloride solution successively and dried over anhydrous magnesium sulfate. The solvent was removed under reduced pressure and the residues was subjected to column chromatography on silica gel [eluted with n-hexane/ethyl acetate (40:1) mixture] to obtain 4.17 g of the desired compound (E/Z=ca. 1/1).

$^1$H-NMR (in CDCl$_3$, TMS as an internal standard).

δ (ppm) 3.80, 3.82 (s, 3H); 6.42, 6.92 (bs 1H); 7.20—7.38 (m, 4H).

(iii) Synthesis of 2-(4-chlorophenyl)-3,3,3-trifluoropropanal

Under a nitrogen atmosphere, 10 ml of 70% perchloric acid was added to a solution of 4.17 g of 2-(4-chlorophenyl)- 3,3,3-trifluoropropenyl methyl ether in 30 ml of diethyl ether at 0° to 5° C. The reaction solution was stirred at room temperature for 14 hours. The reaction mixture was poured into ice water and extracted twice with diethyl ether. The ether layers were combined and washed with saturated sodium bisulfate solution and saturated sodium chloride solution successively and dried over anhydrous magnesium sulfate. The solvent was removed under reduced pressure to obtain 3.67 g of the desired crude compound.

$^1$H-NMR (in CDCl$_3$, TMS as an internal standard).

δ (ppm) 4.25 (dq, 1H).

$^{19}$H-NMR (in CDCl$_3$, CF$_3$COOH as an external standard).

δ (ppm) 14.4 (bd, J=10 Hz, J=3 Hz).

(iv) Synthesis of 2-(4-chlorophenyl)-3,3,3-trifluoropropanol

Into a solution of 3.67 g of 2-(4-chlorophenyl)-3,3,3-trifluoropropanal obtained in the above in 30 ml of THF and 3 ml of water, 0.70 g of sodium borohydride was added with ice-cooling. The reaction solution was stirred at room temperature for 1 hour and poured into ice water and extracted with ethyl acetate. The water layer was adjusted up to pH 4 with dilute HCl and extracted with ethyl acetate again. The ethyl acetate layers were combined and washed with saturated sodium chloride solution and dried over anhydrous magnesium sulfate. The solvent was removed under reduced pressure and the residue was subjected to column chromatography on silica gel [eluted with n-hexane/ethyl acetate (5:1) mixture] to obtain 1.80 g of the desired compound.

$^1$H-NMR (in CDCl$_3$, TMS as an internal standard).

δ (ppm) 1.98 (bt, 1H), 3.30–4.30 (m, 3H), 7.81 (bs, 4H).

$^{19}$F-NMR (in CDCl$_3$, CF$_3$COOH as an external standard).

δ (ppm) +13.3 (dd, J=10 Hz).

EXAMPLE 21

Synthesis of 2-(4-ethylphenyl)-3,3,3-trifluoropropanal (i) Synthesis of 2-(4-ethylphenyl-3,3,3-trifluoropropenyl methyl ether Under a nitrogen atmosphere, 49.5 ml of n-butyllithium/hexane solution (1.2M solution) was added to a solution of 25.5 g of methoxymethyltriphenylphosphonium chloride in 160 ml of dry THF at −60° C. The reaction solution was stirred at −60° C. for 30 minutes and at −20° C. for 30 minutes. A solution of 10.0 g of 4-ethyl-α,α,α-trifluoroacetophenone in 10 ml of dry THF was slowly added to the reaction solution at −60° C. The reaction solution was stirred at −60° C. for 1 hour and at room temperature for 14 hours. Thereafter, 200 ml of n-hexane was added to the reaction mixture and insoluble materials were filtered out. The filtrate was washed with dilute HCl-ice water and saturated sodium chloride solution successively and dried over anhydrous magnesium sulfate. The solvent was removed under reduced pressure and the residue was subjected to column chromatography on silica gel [eluted with n-hexane/ethyl acetate (30:1) mixture] to obtain 5.47 g of the desired compound (E/Z=ca. ½).

$^{19}$H-NMR (in CDCl$_3$, TMS as an internal standard).

δ (ppm) 1.24 (t, 3H), 2.65 (bq, 2H), 3.74 and 3.79 (s, 3H), 6.32 and 6.80 (s, m, 1H), 7.00–7.45 (m, 4H).

$^{19}$F-NMR (in CDCl$_3$, CF$_3$COOH as an external standard).

δ (ppm) +19.6 (m) +22.8 (s).

(ii) Synthesis of 2-(4-ethylphenyl)-3,3,3-trifluoropropanal

Under a nitrogen atmosphere, 20 ml of 70% perchloric acid was added to a solution of 5.47 g of 2-(4-ethylphenyl)-3,3,3-trifluoropropenyl methyl ether in 30 ml of diethyl ether at 0° to 5° C. The reaction solution was stirred at room temperature for 6 hours. The reaction mixture was poured into ice water and extracted twice with diethyl ether. The ether layers were combined and washed with saturated sodium bisulfate solution and saturated sodium chloride solution successively and dried over anhydrous magnesium sulfate. The solvent was removed under a reduced pressure to obtain 4.80 g of the desired crude compound.

$^1$H-NMR (in CDCl$_3$, TMS as an internal standard).

δ (ppm) 1.29 (t, 3H), 2.71 (q, 2H), 4.25 (dq, 1H), 7.10–7.45 (m, 4H), 9.65–9.85 (m, 1H).

$^{19}$F-NMR (in CDCl$_3$, CF$_3$COOH as an external standard).

δ (ppm) +14.9 (dd, J=10 Hz, J=3 Hz).

EXAMPLE 22

Synthesis of 2-(3,4-methylenedioxyphenyl)-3,3,3-trifluoropropanal

(i) Synthesis of ethyl 3-(3,4-methylenedioxyphenyl)-2,3-epoxy-4,4,4-trifluorobutyrate Under a nitrogen atmosphere, 16.2 g of potassium t-butoxide in 70 ml of dry dimethoxyethane was added to a solution of 15.6 g of 3,4-methylendioxy-α,α,α-trifluoroacetophenone and 17.6 g of ethyl chloroacetate in 80 ml of dry dimethoxyethane with ice-cooling. The reaction solution was stirred at room temperature for 16 hours. Thereafter, the reaction mixture was poured into ice water and extracted twice with diethyl ether. The ether layers were combined, washed with saturated sodium chloride solution and dried over anhydrous magnesium sulfate. The solvent was removed under a reduced pressure to obtain 24.0 g of the desired crude product.

$^1$H-NMR (in CDCl$_3$, TMS as an internal standard).

δ (ppm) 1.02 (t, 3H), 4.00 (s, 1H), 5.90 (s, 2H), 6.50–7.00 (m, 3H).

(ii) Synthesis of 2-(3,4-methylenedioxyphenyl)-3,3,3-trifluoropropanal

Into a solution of 9.5 g of potassium hydroxide in 80 ml of ethanol and 20 ml of water, 24.0 g of ethyl 3-(3,4-methylenedioxyphenyl)-2,3-epoxy-4,4,4-trifluorobutyrate was added with ice-cooling. The reaction solution was stirred at room temperature for 17 hours. Thereafter, the reaction solution was poured into ice water. The resulting solution was washed with diethyl ether and adjusted to pH 2 with 10% HCl and extracted twice with ethyl acetate. The ethyl acetate layers were combined and washed with saturated sodium chloride solution and dried over anhydrous magnesium sulfate. The solvent was removed under a reduced pressure and the residue was subjected to distillation under a reduced pressure by heating in an oil bath (140°–160° C.) to obtain 7.7 g of the desired aldehyde (b.p. 121°–122° C./18 mmHg).

$^1$H-NMR (in CDCl$_3$, TMS as an internal standard).

δ (ppm) 3.84–4.30 (m, 1H), 5.91 (s, 2H), 6.70 (m, 3H), 9.62 (m, 1H).

$^{19}$F-NMR (in CDCl$_3$, CF$_3$COOH as an external standard).

δ (ppm) +13.5 (dd, J=9.6 Hz, J=2.5 Hz).

EXAMPLE 23

Synthesis of 2-(4-trifluoromethylphenyl)-3,3,3-trifluoropropanal

(i) Synthesis of 2-(4-trifluoromethylphenyl)-3,3,3-trifluoropropenyl methyl ether Under a nitrogen atmosphere, 25.0 ml of n-butyllithium/hexane solution (1.2M solution) was added to a solution of 12.7 g of methoxymethyltriphenylphosphonium chloride in 100 ml of dry THF at −60° C. The reaction solution was stirred at −60° C. for 30 minutes and at −20° C. for 30 minutes. A solution of 6.0 of 4-trifluoromethyl-α,α,α-trifluoroacetophenone in 10 ml of dry THF was slowly added to the reaction solution at −60° C. The reaction solution was stirred at −60° C. for 1 hour and at room temperature for 14 hours. Thereafter, 150 ml of n-hexane was added to the reaction mixture and insoluble materials were filtered out. The filtrate was washed with dilute HCl-ice water and saturated sodium chloride solution successively and dried over anhydrous magnesium sulfate. The solvent was removed under reduced pressure and 6.1 g of the crude product (E/Z=ca. 1/1) was obtained.

$^1$H-NMR (in CDCl$_3$, TMS as an internal standard).

δ (ppm) 3.79, 383 ( s, 3H), 5.46–6.95 (s, m, 1H), 7.20–7.80 (m, 4H).

(ii) Synthesis of 2-(4-trifluoromethylphenyl)-3,3,3-trifluoropropanal

Under a nitrogen atmosphere, 10 ml of 70% perchloric acid was added to a solution of 6.1 g of 2-(4-trifluoromethylphenyl)-3,3,3-trifluoropropenyl methyl ether in 20 ml of diethyl ether at 0° to 5° C. The reaction solution was stirred at room temperature for 14 hours. The reaction mixture was poured into ice water and extracted twice with diethyl ether. The ether layers were combined and washed with saturated sodium bisulfate solution and saturated sodium chloride solution successively and dried over anhydrous magnesium sulfate. The solvent was removed under reduced pressure to obtain 2.1 g of the desired crude compound.

$^1$H-NMR (in CDCl$_3$, TMS as an internal standard).

δ (ppm) 4.10–4.55 (m, 1H), 7.35–7.75 (m, 4H), 9.78 (m, 1H).

EXAMPLE 24

Synthesis of 2-(4-methylphenyl)-3,3,3-trifluoropropanal

(i) Synthesis of ethyl 3-(4-methylphenyl)-2,3-epoxy-4,4,4-trifluorobutyrate

Under a nitrogen atmosphere, 9.5 g of potassium t-butoxide in 30 ml of dry dimethoxyethane was added to a solution of 8.0 g of 4-methyl-α,α,α-trifluoroacetophenone and 10.4 g of ethyl chloroacetate in 50 ml of dry dimethoxyethane with ice-cooling. The reaction solution was stirred at room temperature for 15 hours. Thereafter, the reaction mixture was poured into ice water and extracted twice with diethyl ether. The ether layers were combined, washed with saturated sodium chloride solution and dried over anhydrous magnesium sulfate. The solvent was removed under a reduced pressure and 12.6 g of the crude product was obtained.

¹H-NMR (in CDCl₃, TMS as in an internal standard).

δ (ppm) 0.85 (t, 3H), 2.25 (s, 3H), 3.70–4.20 (m, 3H), 7.00–7.40 (ABq, 4H).

¹⁹F-NMR (in CDCl₃, CF₃COOH as an external standard).

δ (ppm) +4.8 (s).

(ii) Synthesis of 2-(4-methylphenyl)-3,3,3-trifluoropropanal

Into a solution of 4.8 g of potassium hydroxide in 20 ml of ethanol and 5 ml of water, 8.0 g or ethyl 3-(4-methylphenyl)-2,3-epoxy-4,4,4-trifluorobutyrate was added with ice-cooling. The reaction solution was stirred at room temperature for 3 hours. Thereafter, the reaction solution was poured into ice water. The resulting solution was washed with diethyl ether and adjusted to pH 3 with 10% HCl and extracted twice with diethyl ether. The ether layers were combined and washed with saturated sodium chloride solution and dried over anhydrous magnesium sulfate. The solvent was removed under a reduced pressure and the residue was subjected to distillation under a reduced pressure by heating in an oil bath (140°–160° C.) to obtain 3.0 g of the desired aldehyde (b.p. 110°–120° C./110–120 mmHg).

¹H-NMR (in CDCl₃, TMS as an internal standard).

δ (ppm) 2.31 (s, 3H), 3.90–4.40 (m, 1H), 7.31 (m, 4H), 9.60 (m, 1H).

¹⁹F-NMR (in CDCl₃, CF₃COOH as an external standard).

δ (ppm) +13.8 (dd, J=9.5 Hz, J=2.5 Hz).

EXAMPLE 25

Synthesis of 2-(4-ethoxyphenyl(-3,3,3-trifluoropropanal

(i) Synthesis of ethyl 3-(4-ethoxyphenyl)-2,3-epoxy-4,4,4-trifluorobutyrate Under a nitrogen atmosphere, a solution of 10.0 g of 4-ethoxy-α,α,α-trifluoroacetophenone and 7.87 g of ethyl chloroacetate in 20 l of dry ethanol was added at −10° C. to the sodium ethoxide solution prepared by dissolving 1.58 g of sodium in 50 ml of dry ethanol. The reaction solution was stirred with ice-cooling for 3 hrs and at room temperature for 16 hrs. Thereafter the reaction mixture was poured into ice water and extracted twice with diethyl ether. The ether layers were combined, washed with saturated sodium chloride solution and dried over anhydrous magnesium sulfate. The solvent was removed under a reduced pressure and 7.81 g of the desired compound was obtained by distillation under a reduced pressure.

b.p. 110°–130° C. (0.6 mmHg).

(ii) Synthesis of 2-(4-ethoxyphenyl)-3,3,3-trifluoropropanol

The desired compound was obtained from ethyl 3-(4-ethoxyphenyl)-2,3-epoxy-4,4,4-trifluorobutyrate according to the procedures in example 19-iii).

Examples of the alcohol compound represented by the formula (III) produced above and those of the aldehyde compound represented by the formula (IV) and (IV)' produced above will be given in Table 2, and Table 3, respectively.

TABLE 2

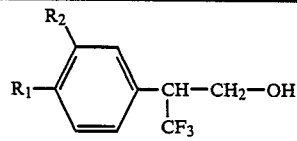

| R₁ | R₂ | ¹H—NMR δ (ppm) | ¹⁹F—NMR δ (ppm) |
|---|---|---|---|
| OCH₂CH₃ | H | 1.40 (t, 3H), 1.98 (bs, 1H), 3.51–4.25 (m, 3H), 4.02 (q, 2H), 6.70–7.40 (m, 4H) | +12.0 (bd, J=10 Hz) |
| Cl | H | 1.98 (bt, 1H), 3.30–4.30 (m, 3H) 7.81 (bs, 4H) | +13.3 (bd, J=10 Hz) |
| F | H | 1.75 (bt, 1H), 3.05–4.20 (m, 3H) 6.65–7.40 (m, 4H) | +12.6 (bd, 3F, J=10 Hz) −33.5 (m, 1F) |
| —OCH₂O— | | 1.75 (bs, 1H), 3.20–4.10 (m, 3H) 5.88 (s, 2H), 6.69 (bs, 3H) | +13.2 (d, J=9.5 Hz) |
| CH₂CH₃ | H | 1.25 (t, 3H), 2.71 (q, 2H) 3.25–4.20 (m, 3H), 7.20 (s, 4H) | +13.2 (bd, J=10 Hz) |
| CF₃ | H | 2.18 (bs, 1H), 3.30–4.30 (m, 3H) 7.40–7.78 (m, 4H) | +13.6 (d, 3F, J=9.5 Hz) +17.8 (s, 3F) |
| OCH₃ | H | 1.22 (t, 3H), 2.10 (bs, 1H) 3.20–4.25 (m, 3H), 3.74 (s, 3H) 6.75–7.25 (m, 4H) | +12.5 (d, J=9.8 Hz) |
| OCH(CH₃)₂ | H | 1.30 (d, 6H), 1.80 (bs, 1H), 3.20–4.20 (m, 3H), 4.50 (m, 1H) 6.73–7.24 (m, 4H) | +12.0 (d, J=9.5 Hz) |
| —CH₂CH₂CH₂— | | 1.80–2.28 (m, 3H), 2.85 (t, 4H) 3.20–4.20 (m, 3H), 6.85–7.20 (m, 3H) | +12.9 (d, J=10 Hz) |
| OCH₂CH=CH₂ | H | 1.90 (bs, 1H), 3.20–4.20 (m, 3H) 4.41–4.55 (m, 2H), 5.15–5.50 (m, 2H) 5.75–6.35 (m, 1H), 6.80–7.28 (m, 4H) | +12.1 (d, J=9.6 Hz) |
| OCH₂CH₃ | Cl | 1.42 (t, 3H), 1.70–2.10 (b, 1H) 3.10–4.30 (m, 3H), 4.08 (q, 2H), 6.80–7.40 (m, 3H) | +12.8 (d, J=10 Hz) |
| Br | H | 2.05 (bs, 1H), 3.20–4.20 (m, 3H) 7.15–7.63 (m, 4H) | +12.9 (d, J=9.5 Hz) |
| H | CF₃ | 1.90 (s, 1H), 3.20–4.20 (m, 3H) | +14.0 (d, 3F, J=9.5 Hz) +17.5 (s, 3F) |
| CH₃ | H | 1.98 (bs, 1H), 2.32 (s, 3H), | +11.9 (d, J=9.6 Hz) |

TABLE 2-continued

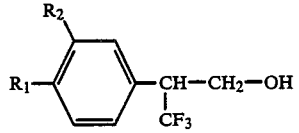

| $R_1$ | $R_2$ | $^1H$—NMR δ (ppm) | $^{19}F$—NMR δ (ppm) |
|---|---|---|---|
| —OCH(CH$_3$)CH$_2$— | | 3.20–4.20 (m, 3H), 7.15 (s, 4H)<br>1.45 (d, 3H), 1.80 (b, 1H) | +13.3 (d, J=9.6 Hz) |
| —OC(CH$_3$)$_2$CH$_2$— | | 2.70–4.20 (m, 5H), 4.60–5.10 (m, 1H)<br>6.60–6.90 (m, 3H)<br>1.48 (s, 6H), 1.85 (b, 1H)<br>3.00 (s, 2H), 3.30–4.35 (m, 3H),<br>6.60–7.00 (m, 3H) | +13.7 (d, J=9.8 Hz) |
| CH$_2$CH=CH$_2$ | H | 2.10 (b, 1H), 3.35 (bd, 2H),<br>3.30–4.15 (m, 3H), 4.80–5.30 (m, 2H),<br>5.65–6.30 (m, 1H) | +12.8 (d, J=10 Hz) |

TABLE 3

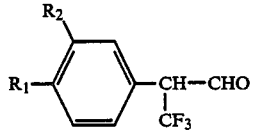

| $R_1$ | $R_2$ | $^1H$—NMR δ (ppm) | $^{19}F$—NMR δ (ppm) |
|---|---|---|---|
| CH$_3$CH$_2$O | H | 1.41 (t, 3H), 4.08 (q, 2H),<br>3.96–4.50 (m, 1H), 6.90–7.45 (m, 4H),<br>9.70–9.90 (m, 1H) | +14.3 (dd, J=10Hz,<br>J=3Hz) |
| Cl | H | 4.25 (dq, 1H), 7.12–7.50 (m, 4H),<br>9.70–9.90 (m, 1H) | +14.4 (dd, J=10Hz,<br>J=3Hz) |
| F | H | 4.00–4.48 (m, 1H), 9.65–9.85 (m, 1H) | +14.6 (dd, J=9.6Hz,<br>J=3Hz) |
| Br | H | 4.00–4.49 (m, 1H), 9.78 (m, 1H) | +14.4 (dd, J=2.5Hz,<br>J=9.7Hz) |
| —OCH$_2$O— | | 3.85–4.30 (m, 1H), 5.91 (s, 2H)<br>6.70 (m, 3H), 9.62 (m, 1H) | +13.5 (dd, J=2.5Hz,<br>J=9.6Hz) |
| —CH$_2$CH$_2$CH$_2$— | | 1.90–2.26 (m, 2H), 2.74–2.96 (m, 4H)<br>3.80–4.25 (m, 1H), 7.06 (m, 3H),<br>9.60 (m, 1H) | +14.9 (dd, J=3Hz,<br>J=10 Hz) |
| CH$_3$O | H | 3.72 (s, 3H), 3.94–4.42 (m, 1H)<br>9.65 (m, 1H) | +13.0 (dd, J=2.5 Hz,<br>J=9.6Hz) |
| CH$_3$CH$_2$O | Cl | 1.42 (t, 3H), 3.88–4.40 (m, 3H),<br>6.75–7.45 (m, 3H), 9.65–9.85 (m, 1H) | +14.7 (dd, J=10Hz,<br>J=3Hz) |
| CH$_3$CH$_2$ | H | 1.29 (t, 3H), 2.71 (q, 2H), 4.25 (dq, 1H)<br>7.10–7.45 (m, 4H), 9.65–9.85 (m, 1H) | +14.9 (dd, J=10Hz,<br>J=3Hz) |
| —OCH(CH$_3$)CH$_2$— | | 1.44 (d, 3H), 2.50–3.50 (m, 2H)<br>3.90–4.40 (m, 1H), 9.80 (m, 1H) | +14.4 (dd, J=3.0Hz,<br>J=10Hz) |
| H | CF$_3$ | 4.00–4.50 (m, 1H), 7.15–7.70 (m, 3H)<br>9.70 (m, 1H) | +14.5 (dd, J=3.0Hz,<br>J=10Hz)<br>+17.7 (s) |
| —OC(CH$_3$)$_2$CH$_2$— | | 1.46 (s, 6H), 3.00 (s, 2H)<br>3.95–4.50 (m, 1H), 6.65–7.00 (m, 3H)<br>9.70 (m, 1H) | +14.2 (dd, J=3.0Hz,<br>J=10Hz) |
| CH$_3$ | H | 2.31 (s, 3H), 3.90–4.40 (m, 1H)<br>7.13 (m, 4H), 9.60 (m, 1H) | +13.8 (dd, J=2.5Hz,<br>J=9.5 Hz) |
| C(CH$_3$)$_3$ | H | 1.31 (s, 9H), 3.90–4.40 (m, 1H)<br>7.25 (m, 4H), 9.64 (m, 1H) | +13.9 (dd, J=2.5Hz,<br>J=9.5Hz) |
| CF$_3$ | H | 4.10–4.55 (m, 1H), 7.35–7.75 (m, 4H)<br>9.78 (m, 1H) | +14.8 (dd, J=9.5Hz,<br>J=2.5Hz)<br>+17.7 (s) |
| CH$_2$CH=CH$_2$ | H | 3.40 (bd, 2H), 3.85–4.40 (m, 1H)<br>4.80–5.30 (m, 2H), 5.70–6.35 (m, 1H)<br>9.85 (m, 1H) | 14.0 (dd, J=3Hz,<br>J=10Hz) |
| OCH$_2$CH=CH$_2$ | H | 3.90–4.40 (m, 1H), 4.45 (bd, 2H)<br>5.10–6.30 (m, 3H), 9.80 (m, 1H) | +14.1 (dd, J=3.0Hz,<br>J=10Hz) |

When the present compounds are used as an active ingredient for an insecticidal and/or acaricidal composition, they may be used as it is without adding any other ingredients. Generally, however, they are formulated into emulsifiable concentrates, wettable powders, dusts, granules, oil sprays, aerosols, heating fumigants (e.g. mosquito coils, electric mosquito mats), foggings, non-heating fumigants, poisonous baits, etc. by mixing with solid carriers, liquid carriers, gaseous carriers, surface active agents, other auxiliaries for formulation, baits, etc., or impregnating into bases such as mosquito coil carrier, mat, etc.

These preparations contain 0.01 to 95% by weight of the present compound as an active ingredient.

The solid carrier includes for example fine powders or granules of kaolin clay, attapulgite clay, bentonite, terra alba, pyrophylite, talc, diatomaceous earth, calcite, corn stalk powder, walnut shell powder, urea, ammonium sulfate, synthetic hydrated silicon dioxide and the like. The liquid carrier includes for example aliphatic hydrocarbons (e.g. kerosene), aromatic hydrocarbons (e.g. toluene, xylene, methylnaphthalene), halogenated hydrocarbons (e.g. dichloroethane, trichloroethylene, carbon tetrachloride), alcohols (e.g. methanol, ethanol, isopropanol, ethylene glycol, cellosolve), ketones (e.g. acetone, methyl ethyl ketone, cyclohexanone, isophorone), ethers (e.g. diethyl ether, dioxane, tetrahydrofuran), esters (e.g. ethyl acetate), nitriles (e.g. acetonitrile, isobutyronitrile), acid amides (e.g. dimethylformamide, dimethylacetamide), dimethyl sulfoxide, vegetable oils (e.g. soybean oil, cotton seed oil), and the like. The gaseous carrier includes for example freon gas, LPG (liquefied petroleum gas), dimethyl ether and the like. The surface active agent used for emulsification, dispersion, wetting, etc. includes for example anionic surface active agents such as the salt of alkyl sulfates, alkyl(aryl) sulfonates, diakyl sulfosuccinates, the salt of polyoxyethylene alkylaryl ether phosphoric acid ester, naphthalenesulfonic acid/formalin condensates, etc., and nonionic surface active agents such as polyoxyethylene alkyl ether, polyoxyethylene polyoxypropylene block copolymers, sorbitan fatty acid esters, polyoxyethylene sorbitan fatty acid esters, etc. The auxiliary for formulation such as sticking agents, dispersing agents, etc. includes for example lignoxulfonates, alginates, polyvinyl alcohol, gum arabic, molasses, casein, gelatin, CMC (carboxymethyl cellulose), pine oil, agar, etc. The stabilizer includes for example alkyl phosphates [e.g. PAP (isopropyl acid phosphate), TCP (tricresyl phosphate)], vegetable oils, epoxidized oil, the foregoing surface active agents, antioxidants (e.g. BHT, BHA), fatty acid salts (e.g. sodium oleate, calcium stearate), fatty acid esters (e.g. methyl oleate, methyl stearate) and the like.

Next, formulation examples will be shown. The present compounds are shown by Compound No. described in Table 1. Parts in the examples are by weight.

Formulation example 1

0.2 Part of each of the present compounds (1), (2), (3), (9), (10) (11), (39) and (1)-A, 2 parts of xylene and 97.8 parts of kerosene are mixed to obtain the oil spray of each compound.

Formulation example 2

Ten parts of each of the present compounds (1) to (53) and (1)-A, 14 parts of polyoxyethylene styrylphenyl ether, 6 parts of calcium dodecylbenzenesulfonate and 70 parts of xylene are well mixed to obtain the emulsifiable concentrate of each compound.

Formulation example 3

Twenty parts of each of the present compounds (1), (4), (9), (10), (12), (40) and (1)-A, 10 parts of fenitrothion, 3 parts of calcium lignosulfonate, 2 parts of sodium lauryl sulfate and 65 parts of synthetic hydrated silicon dioxide are well pulverized and mixed together to obtain the wettable powder of each compound.

Formulation example 4

One part of each of the present compounds (2), (5), (9), (10), (13), (41) and (1)-A, 2 parts of carbaryl, 87 parts of kaolin clay and 10 parts of talc are well pulverized and mixed together to obtain the dust of each compound.

Formulation example 5

Five parts of each of the present compounds (1), (6), (9), (10), (20), (42) and (1)-A, 1 part of synthetic hydrated silicon dioxide, 2 parts of calcium lignosulfonate, 30 parts of bentonite and 62 parts of kaolin clay are well pulverized and mixed thoroughly, kneaded well with water, granulated and then dried to obtain the granules of each compound.

Formulation example 6

0.05 Part of each of the present compounds (2), (7), (9), (10), (27), (46) and (1)-A, 0.2 part of tetramethrin, 0.05 part of resmethrin, 7 parts of xylene and 32.7 parts of deodorized kerosene are well mixed into a solution. The solution is filled in an aerosol container, and after attaching a valve portion to the container, 60 parts of a propellant (liquefied petroleum gas) is charged therein through the valve under pressure to obtain the aerosol of each compound.

Formulation example 7

0.3 Gram of each of the present compounds (1), (8), (9), (10), (30), (47) and (1)-A and 0.3 g of the d-trans chrysanthemate of allethrin are dissolved in 20 ml of methanol. This solution and 99.4 g of a mosquito coiler carrier, which is a 3:5:1 mixture of Tabu powder, Pyrethrum marc and wood powder, are uniformly mixed with stirring. After evaporating methanol, 150 ml of water is added to the residue, and the mixture is well kneaded, shaped and dried to obtain the mosquito coil of each compound.

These preparations are used as it is or as diluted solutions with water. Also, they may be used in mixture with other insecticides, acaricides, nematocides, fungicides, herbicides, plant growth regulators, fertilizers, soil conditioners and the like.

When the present compound is used as an insecticidal and/or acaricidal composition, its dosage rate is generally 50 to 5000 g per hectare. When emulsifiable concentrates, wettable powders, etc. are used as aqueous dilute solutions, the application concentration of the compound is 10 to 1000 ppm. Dusts, granules, oil sprays, aerosols, etc. are used as it is without dilution.

Next, test examples will be shown. The present compounds are shown by Compound No. in Table 1, and compounds used as a control are shown by Compound symbol in Table 4.

TABLE 4

| Compound symbol | Structural formula | Remarks |
|---|---|---|
| (A) | 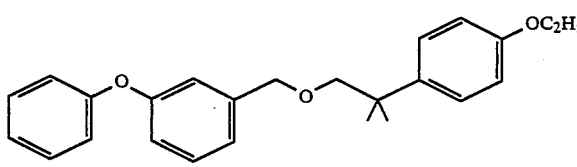 | Compound described in Japanese Patent Application Kokai (Laid-Open) No. Sho 57-72928 |

TABLE 4-continued

| Compound symbol | Structural formula | Remarks |
|---|---|---|
| (B) | [phenyl ring with O-C(=O)-NHCH$_3$ group and sec-butyl substituent] | BPMC |
| (C) | (CH$_3$O)$_2$P(=O)-S-CH(COOC$_2$H$_5$)-CH$_2$-COOC$_2$H$_5$ | Malathion |
| (D) | Cl-C$_6$H$_3$(CH$_3$)-N=CH-N(CH$_3$)$_2$ | Chlordimeform |

Test example 1

Two milliliters each of the 200-fold aqueous dilute solutions (corresponding to 500 ppm), prepared from the emulsifiable concentrates of the following present compounds obtained according to Formulation example 2, were infiltrated into 13 g of artificial diet for tobacco cutworm (*Spodoptera litura*). The diet was then placed in a polyethylene cup of 11 cm in diameter, and 10 fourth instar larvae of tobacco cutworm were liberated therein. After six days, the dead and alive were examined to calculate the mortality (two replications).

The result is shown in Table 5.

TABLE 5

| Test compound | Mortality (%) | Test compound | Mortality (%) |
|---|---|---|---|
| (1) | 100 | (29) | 100 |
| (2) | 100 | (30) | 100 |
| (3) | 100 | (31) | 100 |
| (4) | 100 | (32) | 100 |
| (5) | 100 | (33) | 100 |
| (6) | 100 | (34) | 100 |
| (7) | 100 | (35) | 100 |
| (8) | 100 | (36) | 100 |
| (9) | 100 | (37) | 100 |
| (10) | 100 | (38) | 100 |
| (11) | 100 | (39) | 100 |
| (12) | 100 | (40) | 100 |
| (13) | 100 | (41) | 100 |
| (14) | 100 | (42) | 100 |
| (15) | 100 | (43) | 100 |
| (16) | 100 | (44) | 100 |
| (17) | 100 | (45) | 100 |
| (18) | 100 | (46) | 100 |
| (19) | 100 | (47) | 100 |
| (20) | 100 | (48) | 100 |
| (21) | 100 | (49) | 100 |
| (22) | 100 | (50) | 100 |
| (23) | 100 | (51) | 100 |
| (24) | 100 | (52) | 100 |
| (25) | 100 | (53) | 100 |
| (26) | 100 | (1)-A | 100 |
| (27) | 100 | No treatment | 5 |
| (28) | 100 | | |

Test example 2

The emulsifiable concentrates of the following present compounds and controls obtained according to Formulation example 2 were each diluted with water to obtain respective 667 times dilution aqueous solutions (corresponding to 150 ppm) containing said compounds, respectively. The culm of rice plant (about 12 cm in length) was dipped for 1 minute in the resulting aqueous dilute solutions. After air-drying, the culm was placed in a glass tube, and 10 adults of a resistant strain of green rice leafhopper (*Nephotettix cincticeps*) were liberated in the tube. After one day, the dead and alive of the adult were examined to calculate the mortality (two replications).

The result is shown in Table 6.

TABLE 6

| Test compound | Mortality (%) | Test compound | Mortality (%) |
|---|---|---|---|
| (1) | 100 | (30) | 100 |
| (2) | 100 | (31) | 100 |
| (3) | 100 | (32) | 100 |
| (4) | 100 | (33) | 100 |
| (5) | 100 | (34) | 100 |
| (6) | 100 | (35) | 100 |
| (7) | 100 | (36) | 100 |
| (8) | 100 | (37) | 100 |
| (9) | 100 | (38) | 100 |
| (10) | 100 | (39) | 100 |
| (11) | 100 | (40) | 100 |
| (12) | 100 | (41) | 100 |
| (13) | 100 | (42) | 100 |
| (14) | 100 | (43) | 100 |
| (15) | 100 | (44) | 100 |
| (16) | 100 | (45) | 100 |
| (17) | 100 | (46) | 100 |
| (18) | 100 | (47) | 100 |
| (19) | 100 | (48) | 100 |
| (20) | 100 | (49) | 100 |
| (21) | 100 | (50) | 100 |
| (22) | 100 | (51) | 100 |
| (23) | 100 | (52) | 100 |
| (24) | 100 | (53) | 100 |
| (25) | 100 | (1)-A | 100 |
| (26) | 100 | (B) | 25 |
| (27) | 100 | (C) | 25 |
| (28) | 100 | No treatment | 10 |
| (29) | 100 | | |

Test example 3

The emulsifiable concentrates of the following present compounds and control obtained according to Formulation example 2 were each diluted with water to obtain respective 2000 times dilution aqueous solutions (corresponding to 50 ppm) containing said compounds, respectively. The culm of rice plant (about 12 cm in length) was dipped for 1 minute in the resulting aqueous dilute solutions. After air-drying, the culm was placed in a glass tube, and 10 adults of brown planthopper (*Nilaparvata lugens*) were liberated in the tube. After one day, the dead and alive of the adult were examined to calculate the mortality (two replications).

The result is shown in Table 7.

TABLE 7

| Test compound | Mortality (%) | Test compound | Mortality (%) |
|---|---|---|---|
| (1) | 100 | (27) | 100 |
| (2) | 100 | (31) | 100 |
| (3) | 100 | (32) | 100 |
| (4) | 100 | (36) | 100 |
| (5) | 100 | (51) | 100 |
| (10) | 100 | (1)-A | 100 |
| (13) | 100 | (A) | 20 |
| (15) | 100 | | |
| (16) | 100 | No treatment | 5 |

Test example 4

On the bottom of a polyethylene cup of 5.5 cm in diameter was placed a piece of filter paper of the same size as the bottom, and 0.7 ml each of the 6670 times aqueous dilute solution (corresponding to 15 ppm), which solution was prepared from the emulsifiable concentrates of the following present compounds and controls obtained according to Formulation example 2, was added dropwise to the filter paper. Thirty milligrams of sucrose were uniformly placed on the filter paper as bait. Thereafter, 10 female adults of housefly (*Musca domestica*) were liberated in the cup which was then covered with a lid. After 48 hours, the dead and alive were examined to calculate the mortality (two replications).

The result is shown in Table 8.

TABLE 8

| Test compound | Mortality (%) | Test compound | Mortality (%) |
|---|---|---|---|
| (1) | 100 | (20) | 100 |
| (2) | 100 | (26) | 100 |
| (4) | 100 | (27) | 100 |
| (5) | 100 | (34) | 100 |
| (6) | 100 | (39) | 100 |
| (10) | 100 | (1)-A | 100 |
| (15) | 100 | (A) | 20 |
| (16) | 100 | | |
| (17) | 100 | No treatment | 0 |

Test example 5

The female adults of carmine spider mite (*Tetranychus cinnabarinus*) were put at a rate of 10 adults/leaf on the leaves of potted kidney bean (at the primordial leaf stage) which had elapsed 7 days after sowing, and placed in a constant-temperature room kept at 25° C. After 6 days, the 200-fold aqueous dilute solutions (corresponding to 500 ppm), prepared from the emulsifiable concentrates of the following present compounds and controls prepared according to Formulation example 2, were each sprayed at a rate of 15 ml/pot on a turn table. At the same time, the soil in the pot was treated with 2 ml of each aqueous dilute solution. After 8 days, the degree of damage of the plant by the mite was examined.

Standard for the judgement of the effect:

| — : | No damaged. |
|---|---|
| + : | Slight damage is observed. |

-continued

| ++ : | The same damage as in the untreated plot is observed. |
|---|---|

The result is shown in Table 9.

TABLE 9

| Test compound | Degree of damage | Test compound | Degree of damage |
|---|---|---|---|
| (1) | — | (26) | — |
| (2) | — | (27) | — |
| (3) | — to + | (30) | — |
| (4) | — | (31) | — |
| (5) | — | (32) | — |
| (6) | — to + | (34) | — |
| (7) | — | (36) | — |
| (8) | — | (40) | — |
| (9) | — | (41) | — to + |
| (10) | — | (42) | — to + |
| (11) | — | (46) | — |
| (12) | — | (47) | — to + |
| (14) | — | (49) | — |
| (15) | — | (51) | — |
| (16) | — | (52) | — |
| (17) | — | (53) | — |
| (18) | — to + | (1)-A | — |
| (20) | — | (A) | + to ++ |
| (23) | — | (D) | + |
| (25) | — | No treatment | ++ |

Test example 6

The emulsifiable concentrates of the following present compounds obtained according to Formulation example 2 were each diluted with water to a prescribed concentration, and one ml each of thus prepared solutions was impregnated into the artificial diet for rice stem borer (*Chilo suppressalis*) which had been previously set in polyethylene cups of 5.5 cm in diameter, respectively. Ten larvae of the 10 day-old rice stem borers were liberated thereon. After 8 days, the dead and alive of the larvae were examined to calculate the mortality (two replications).

The result is shown in Table 10.

TABLE 10

| | Concentration (ppm) and mortality (%) | | |
|---|---|---|---|
| Test compound | 5 ppm | 1.5 ppm | 0.5 ppm |
| (1) | 100 | 70 | 5 |
| (1)-A | 100 | 100 | 95 |
| No treatment | | 5 | |

What is claimed is:

1. An ether compound and its optical isomer represented by the formula

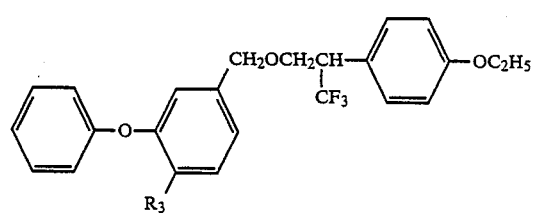

wherein $R_3$ represents a hydrogen or fluorine atom.

2. A compound of the formula,

3. A compound of the formula,

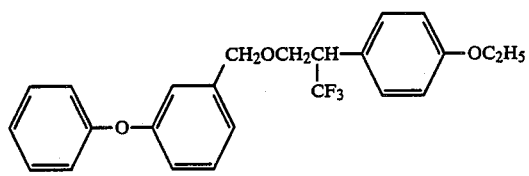

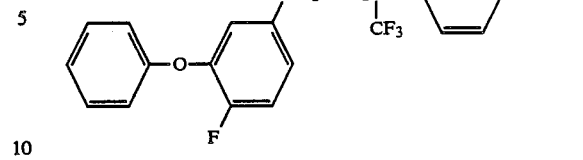

4. A compound of the formula according to claim 2, wherein the compound is an optically active isomer having an (+) optical rotation.

5. The insecticidal and/or acaricidal composition which comprises as an active ingredient an insecticidally and/or acaricidally effective amount of the ether compound according to claim 1 and an inert carrier.

6. A method for controlling an insect and/or an acarid, which comprises applying an insecticidally and/or acaricidally effective amount of the ether compound according to claim 1 to the insect and the acarid.

* * * * *

Notice of Adverse Decisions in Interference

In Interference No. 102,888, involving Patent No. 4,840,971, K. Tsushima, N. Matsuo, Y. Tanabe, T. Yano, M. Hirano, NOVEL ETHER COMPOUND, A PROCESS FOR MANUFACTURING THE SAME, A COMPOSITION CONTAINING THE SAME, AND A USE THEREOF, final judgment adverse to the patentees was rendered July 7, 1992, as to claims 1-6.

*(Official Gazette August 25, 1992.)*